United States Patent
Py et al.

(10) Patent No.: US 9,783,326 B2
(45) Date of Patent: Oct. 10, 2017

(54) ADJUSTABLE FILLING AND SEALING METHOD AND APPARATUS THEREFOR

(71) Applicant: MedInstill Development LLC, New Milford, CT (US)

(72) Inventors: Daniel Py, Larchmont, NY (US); Benoit Adamo, South Salem, NY (US); John Guthy, Oxford, CT (US)

(73) Assignee: MEDINSTILL DEVELOPMENT LLC, New Milford, CT (US)

( * ) Notice: Subject to any disclaimer, the term of this patent is extended or adjusted under 35 U.S.C. 154(b) by 171 days.

(21) Appl. No.: 14/294,403

(22) Filed: Jun. 3, 2014

(65) Prior Publication Data
US 2014/0352265 A1 Dec. 4, 2014

Related U.S. Application Data

(60) Division of application No. 13/352,235, filed on Jan. 17, 2012, now Pat. No. 8,739,838, which is a division
(Continued)

(51) Int. Cl.
| | |
|---|---|
| *B65B 3/00* | (2006.01) |
| *A61L 2/10* | (2006.01) |
| *A61M 5/178* | (2006.01) |
| *B29C 65/00* | (2006.01) |
| *B65B 43/00* | (2006.01) |
| *B65B 51/00* | (2006.01) |

(52) U.S. Cl.
CPC ............... *B65B 3/006* (2013.01); *A61L 2/10* (2013.01); *A61M 5/1782* (2013.01); *B29C 66/80* (2013.01); *B65B 3/003* (2013.01); *B65B 43/00* (2013.01); *B65B 51/00* (2013.01); *Y10T 29/49716* (2015.01)

(58) Field of Classification Search
CPC .......... B65B 37/06; B65B 3/003; B65B 1/22; B65B 55/04; B65B 57/00; B65B 7/00
USPC ............. 141/2, 11, 69, 85, 91, 92, 129, 130, 141/234–237, 329; 53/425, 426, 267, 53/268, 284.5, 561
See application file for complete search history.

(56) References Cited

U.S. PATENT DOCUMENTS

| | | |
|---|---|---|
| 2,193,059 A | 3/1940 | Chapman |
| 2,503,147 A | 4/1950 | Applezweig |

(Continued)

FOREIGN PATENT DOCUMENTS

DE EP 1298062 * 2/2003 ............. B65B 59/02

*Primary Examiner* — Timothy L Maust
(74) *Attorney, Agent, or Firm* — McCarter & English, LLP

(57) ABSTRACT

An assembly includes a support and drive assembly, a first structure and a second structure. The first structure is in operable communication with and supported by the support and drive assembly. The first structure includes at least one filling or needle assembly and is adjustable to receive a plurality of filling or needle assemblies. The second structure is supported by the support and drive assembly. The second structure includes at least one seal assembly and is adjustable to receive a plurality of seal assemblies. A method includes determining a number of containers or vials that are to be filled concurrently and adjusting an assembly to include at least one filling or needle assembly and at least one seal assembly. A number of the filling or needle assemblies and the seal assemblies equals the number of containers or vials.

21 Claims, 27 Drawing Sheets

Related U.S. Application Data of application No. 12/627,655, filed on Nov. 30, 2009, now Pat. No. 8,096,333, which is a continuation of application No. 10/983,178, filed on Nov. 5, 2004, now Pat. No. 7,628,184.

(60) Provisional application No. 60/518,685, filed on Nov. 10, 2003, provisional application No. 60/518,267, filed on Nov. 7, 2003.

(56) References Cited

U.S. PATENT DOCUMENTS

| | | | |
|---|---|---|---|
| 2,562,815 A * | 7/1951 | Oscroft | B65B 3/003 141/165 |
| 3,020,939 A * | 2/1962 | Donofrio | B65B 43/48 141/169 |
| 3,421,840 A | 1/1969 | Pechmann | |
| 3,685,248 A * | 8/1972 | Godelaine | B65B 3/003 141/1 |
| 3,788,519 A | 1/1974 | Mengel | |
| 3,911,976 A * | 10/1975 | Rosen | B65B 57/06 141/180 |
| 4,077,441 A * | 3/1978 | Rosen | B65B 59/00 141/1 |
| 4,528,796 A * | 7/1985 | Lemaire | B67C 7/00 53/268 |
| 4,750,531 A * | 6/1988 | Juenkersfeld | B67C 3/22 141/1 |
| 4,842,028 A | 6/1989 | Kaufman et al. | |
| 4,865,090 A | 9/1989 | Burolla et al. | |
| 5,067,532 A | 11/1991 | Lang et al. | |
| 5,413,000 A | 5/1995 | Stark et al. | |
| 5,425,402 A * | 6/1995 | Pringle | B67C 3/26 141/157 |
| 5,641,004 A | 6/1997 | Py | |
| 5,749,201 A * | 5/1998 | Cochrane | B65D 41/48 430/945 |
| 5,862,840 A | 1/1999 | Hansen | |
| 6,021,824 A | 2/2000 | Larsen et al. | |
| 6,135,172 A | 10/2000 | Féré et al. | |
| 6,189,578 B1 | 2/2001 | Clusserath | |
| 6,544,257 B2 | 4/2003 | Nagase et al. | |
| 6,604,561 B2 | 8/2003 | Py | |
| 6,672,344 B1 * | 1/2004 | Stokes | B01J 19/0046 141/279 |
| 6,684,915 B1 * | 2/2004 | Ver Hage | B67C 3/02 141/2 |
| 7,365,343 B2 | 4/2008 | Thilly et al. | |
| 7,549,275 B2 * | 6/2009 | Monti | B65B 7/28 177/53 |
| 7,628,184 B2 | 12/2009 | Py et al. | |
| 7,707,807 B2 | 5/2010 | Py | |
| 7,937,907 B2 * | 5/2011 | Fleckenstein | B65B 3/003 53/268 |
| 8,919,392 B2 * | 12/2014 | Bullen | B65B 3/003 141/237 |
| 2003/0089743 A1 | 5/2003 | Py et al. | |
| 2003/0159750 A1 | 8/2003 | Py | |
| 2003/0178097 A1 * | 9/2003 | Willstumpf | B65B 3/003 141/329 |
| 2008/0035218 A1 * | 2/2008 | Thilly | B65B 3/003 137/561 R |

* cited by examiner

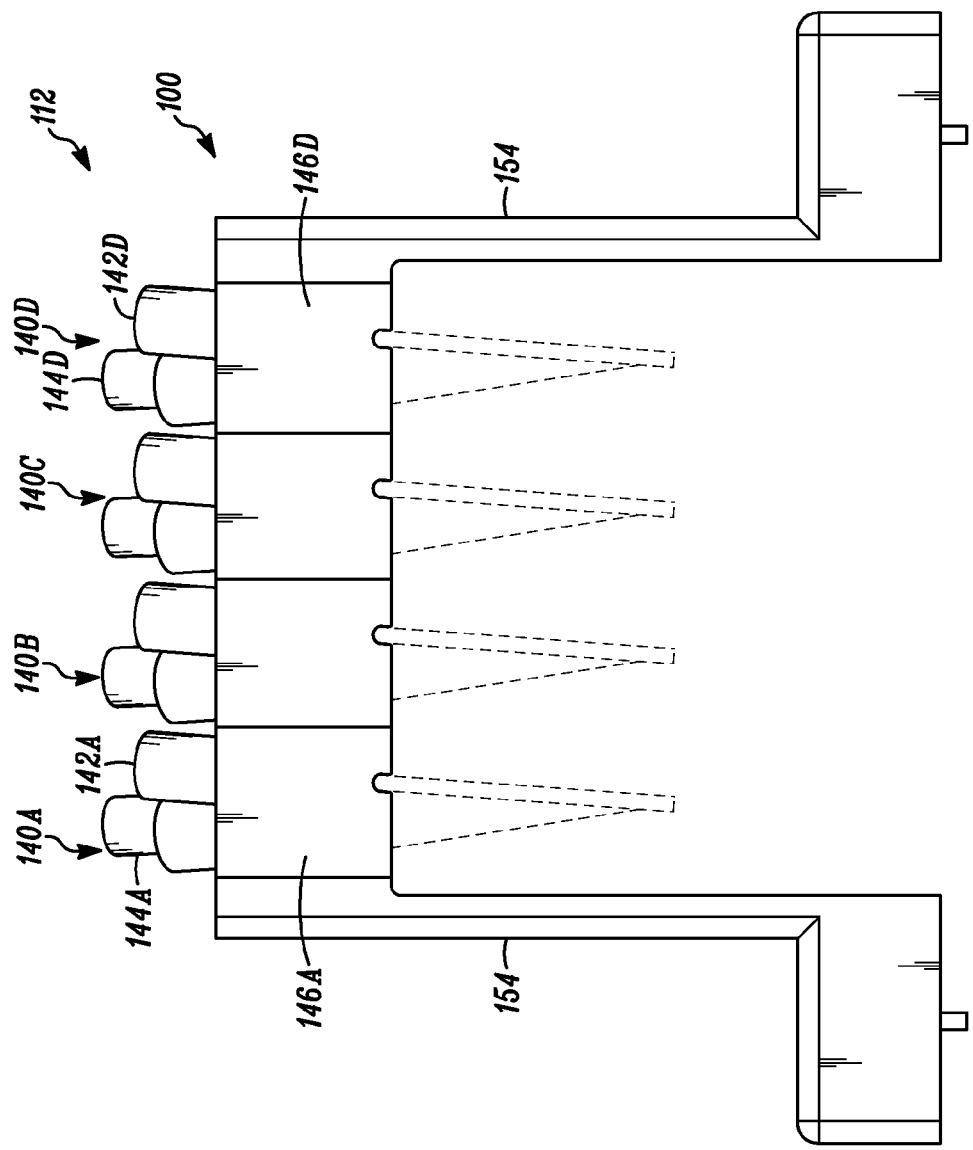

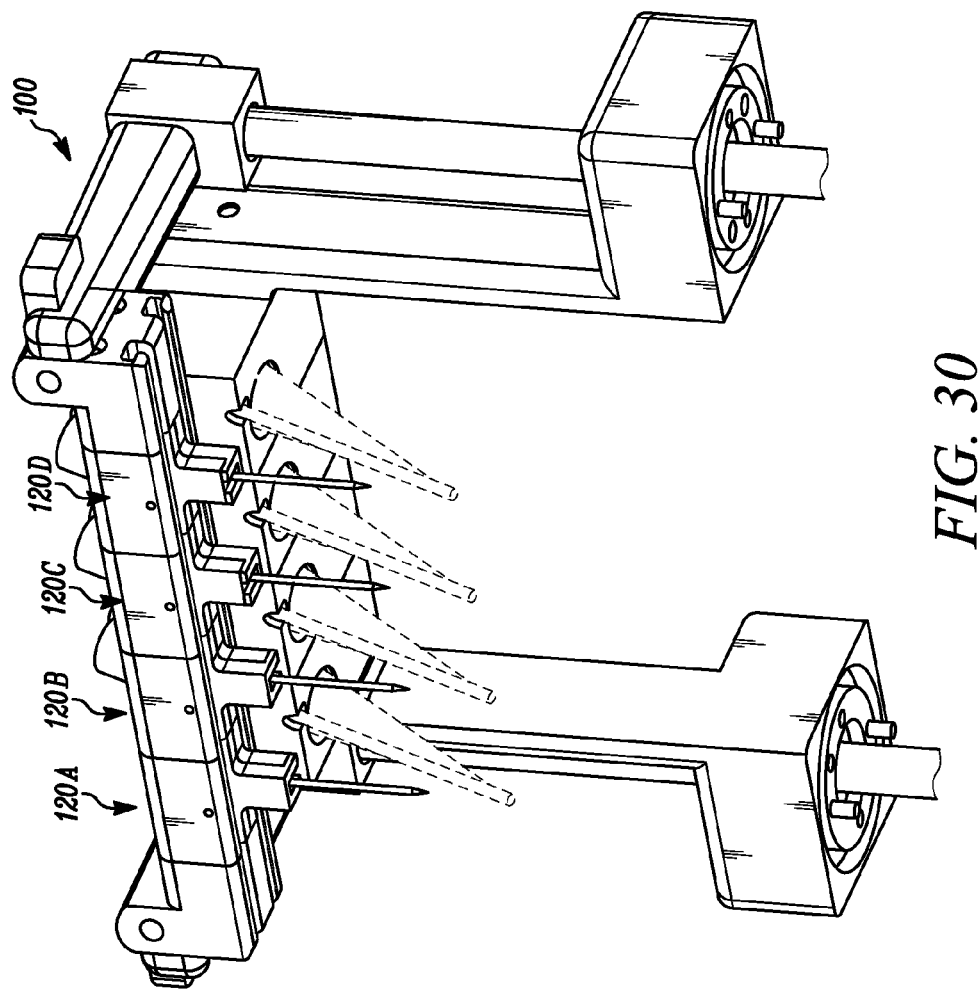

ADJUSTABLE FILLING AND SEALING METHOD AND APPARATUS THEREFOR

CROSS-REFERENCE TO RELATED APPLICATIONS

This patent application is a divisional of U.S. application Ser. No. 13/352,235, filed Jan. 17, 2012, which is a divisional of U.S. application Ser. No. 12/627,655, filed Nov. 30, 2009, now U.S. Pat. No. 8,096,333 issued Jan. 17, 2012, which is continuation of U.S. application Ser. No. 10/973,178, filed Nov. 5, 2004, now U.S. Pat. No. 7,628,184 issued Dec. 8, 2009, claiming the benefit under 35 U.S.C. §119(e) of U.S. Provisional Patent Application Ser. No. 60/518,267, filed Nov. 7, 2003, and U.S. Provisional Patent Application Ser. No. 60/518,685, filed Nov. 10, 2003, all of which are hereby expressly incorporated by reference as part of the present disclosure.

TECHNICAL FIELD

The present invention relates to methods and apparatus for use in filling vials or other containers with medicaments or other substances by temporary introduction of a needle or syringe through a resealable cap or stopper and/or sealing such vials or containers subsequent to filling.

BACKGROUND OF THE INVENTION

Medicaments such as vaccines are often stored in vials prior to use. A typical vial dispenser includes a body defining a storage chamber, a fill opening in fluid communication with the body, and a stopper or cap for sealing the fill opening after filling the storage chamber to hermetically seal the medicament within the dispenser. In order to fill such dispensers with a sterile fluid or other substance, such as a medicament, it is necessary to sterilize the unassembled components of the dispenser, such as by autoclaving the components and/or exposing the components to gamma radiation. The sterilized components then must be filled and assembled in an aseptic isolator of a sterile filling machine. In some cases, the sterilized components are contained within multiple sealed bags or other sterile enclosures for transportation to the sterile filling machine. In other cases, the sterilization equipment is located at the entry to the sterile filling machine. In a filling machine of this type, every component is transferred sterile into the isolator, the storage chamber of the vial is filled with the fluid or other substance, the sterilized stopper is assembled to the vial to plug the fill opening and hermetically seal the fluid or other substance in the vial, and then a crimping ring is assembled to the vial to secure the stopper thereto.

One issue associated with such dispensers, and processes and equipment for filling such dispensers, is that the filling process is time consuming, and the processes and equipment are expensive. Further, the relatively complex nature of the filling processes and equipment can lead to more defectively filled dispensers than otherwise desired. For example, typically there are at least as many sources of failure as there are components. In many cases, there are complex assembly machines for assembling the vials or other dispensers that are located within the aseptic area of the filling machine that must be maintained sterile. This type of machinery can be a significant source of unwanted particles. Further, such isolators are required to maintain sterile air within the barrier enclosure. In closed barrier systems, convection flow is inevitable and thus laminar flow, or substantially laminar flow, cannot be achieved. When operation of an isolator is stopped, a media fill test may have to be performed which can last for several, if not many days, and can lead to repeated interruptions and significant reductions in production output for the pharmaceutical or other product manufacturer that is using the equipment. In order to address such production issues, government-imposed regulations are becoming increasingly sophisticated and are further increasing the cost of already-expensive isolators and like filling equipment. On the other hand, governmental price controls for injectables and vaccines, including, for example, preventative medicines, discourage such major financial investments. Accordingly, there is a concern that fewer companies will be able to afford such increasing levels of investment in sterile filling machines, thus further reducing competition in the injectable and vaccine marketplaces.

SUMMARY OF THE INVENTION

Exemplary embodiments of the invention include an assembly that includes a support and drive assembly, a first structure and a second structure. The first structure is in operable communication with and supported by the support and drive assembly. The first structure includes at least one needle assembly and is adjustable to receive a plurality of needle assemblies. The second structure is supported by the support and drive assembly. The second structure includes at least one seal assembly and is adjustable to receive a plurality of seal assemblies.

Exemplary embodiments of the invention further include a method that includes determining a number of vials that are to be filled concurrently and adjusting an assembly to include at least one needle assembly and at least one seal assembly. A number of the needle assemblies and the seal assemblies equals the number of vials.

BRIEF DESCRIPTION OF THE DRAWINGS

FIG. 26 is a side elevational view of the assembly of FIG. 1 with the needle manifold removed and after adjustment of the sealing and sensing manifold and addition of three additional sealing and sensing assemblies;

FIG. 30 is a perspective view of the assembly of FIG. 29.

DETAILED DESCRIPTION

Figure 1:
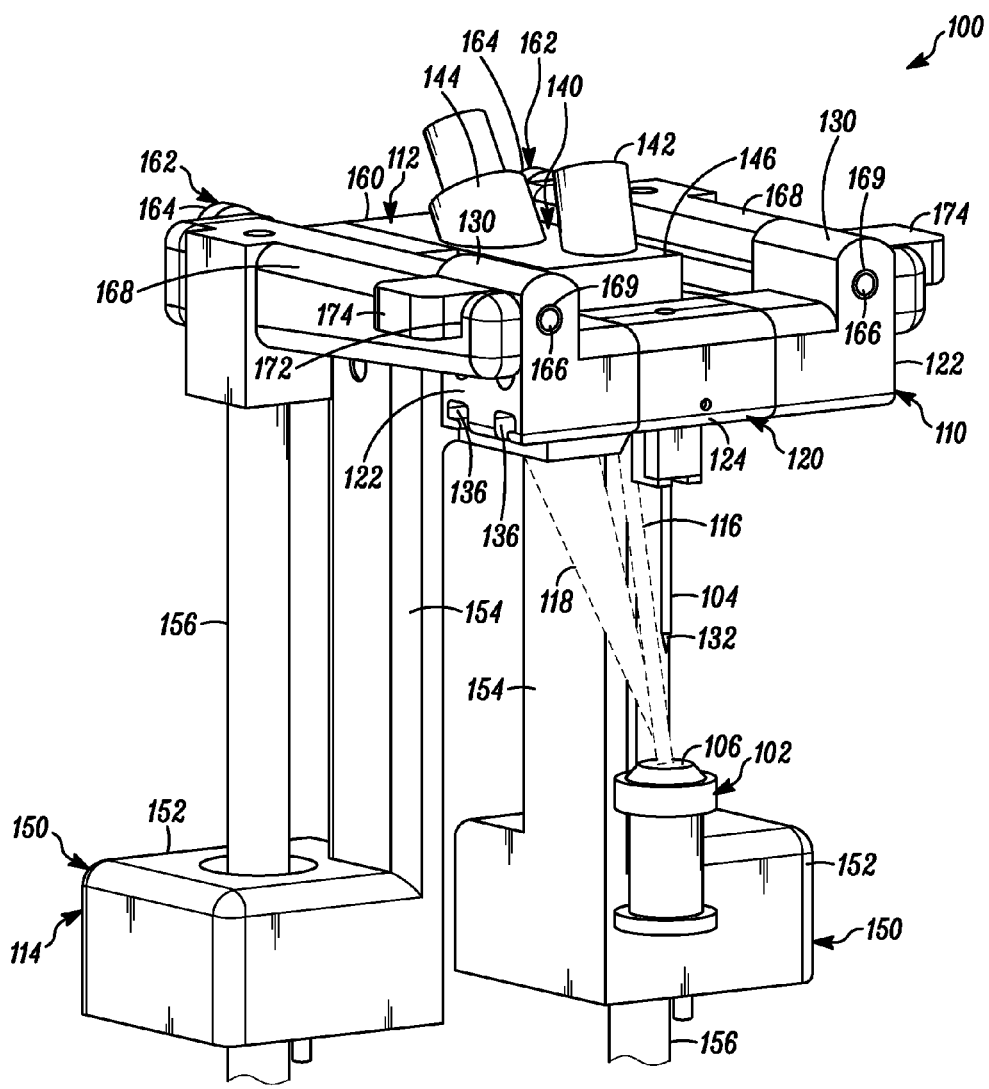
FIG. 1 is a perspective view of one embodiment of a needle filling and laser sealing assembly, a vial or other container to be filled and sealed, and schematic representations of a laser beam provided by the assembly and radiation sensed by the assembly.
Figure 2:
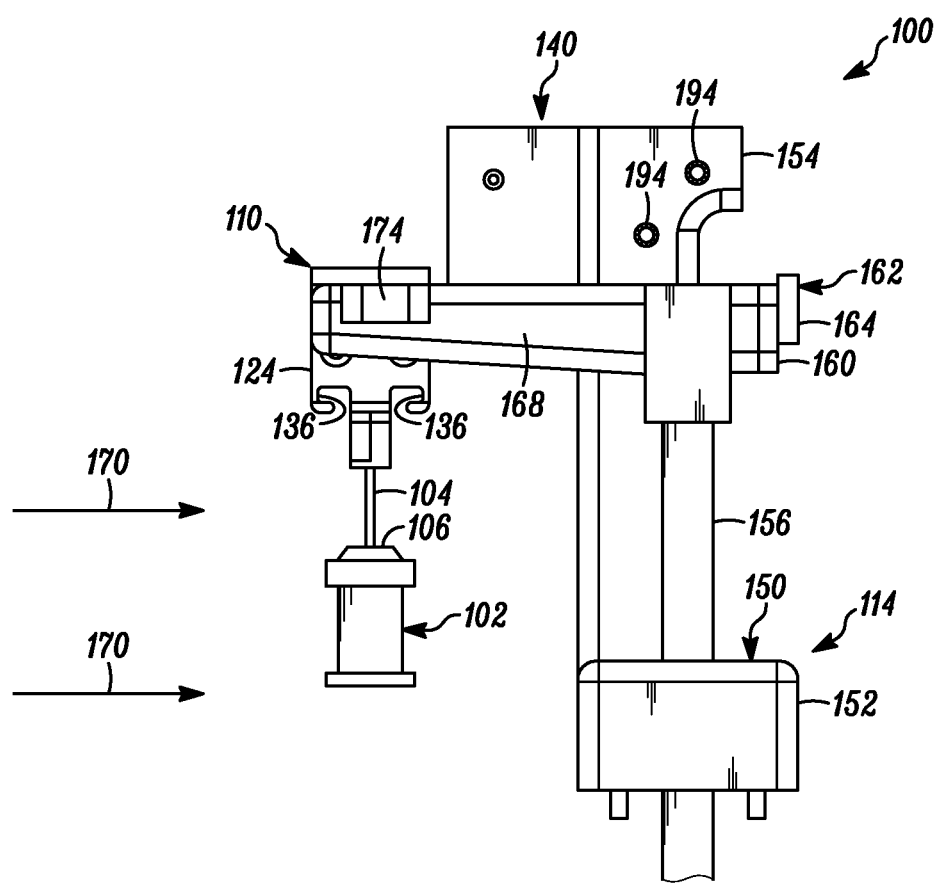
FIG. 2 is a side elevational view of the assembly and vial of FIG. 1, with the needle manifold in a position whereby the needle is inserted into the vial and illustrating the substantially laminar flow of aseptic air laterally over the vials and/or other containers being filled and/or re-sealed.
Figure 3:
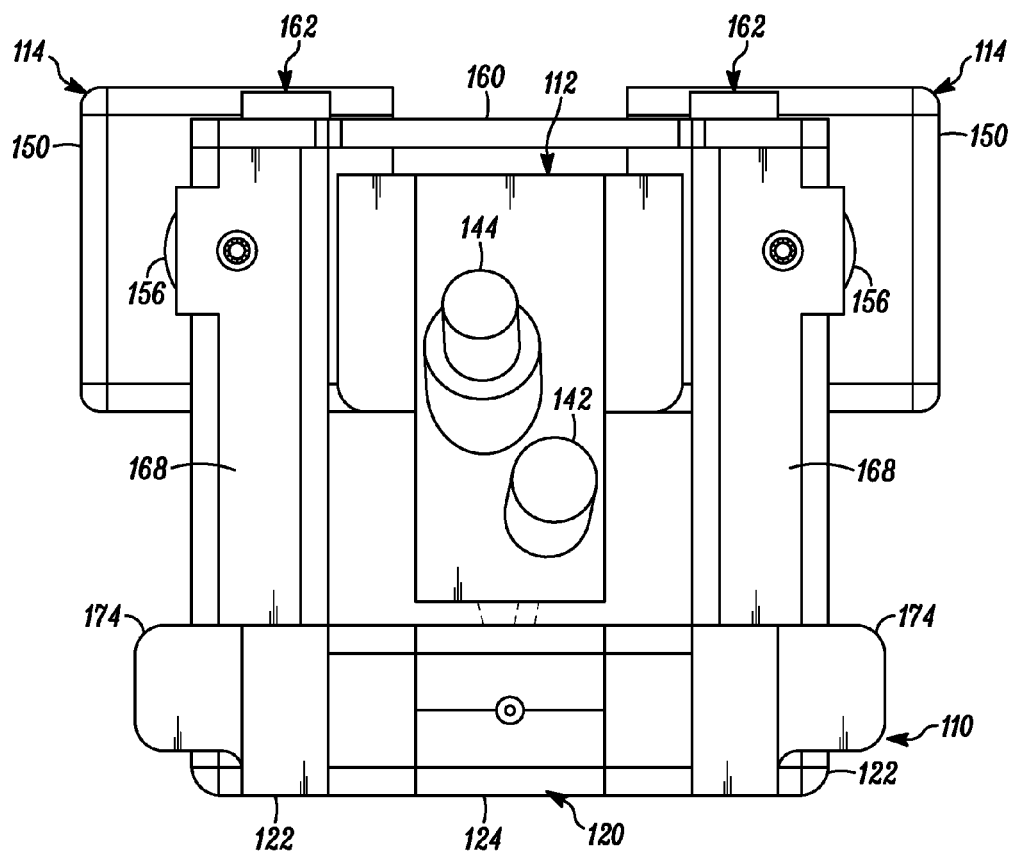
FIG. 3 is a top elevational view of the assembly of FIG. 1.
Figure 4:
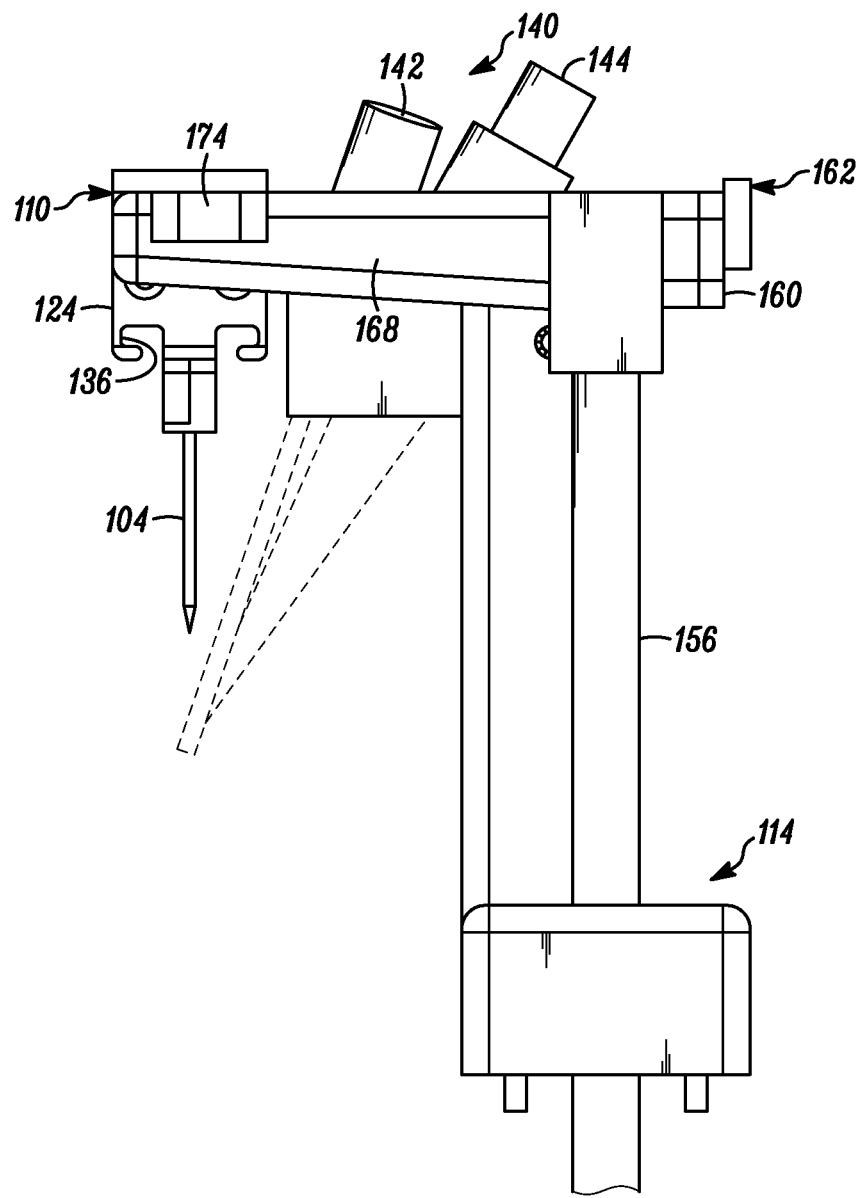
FIG. 4 is another side elevational view of the assembly of FIG. 1, without the vial or container.
Figure 5:
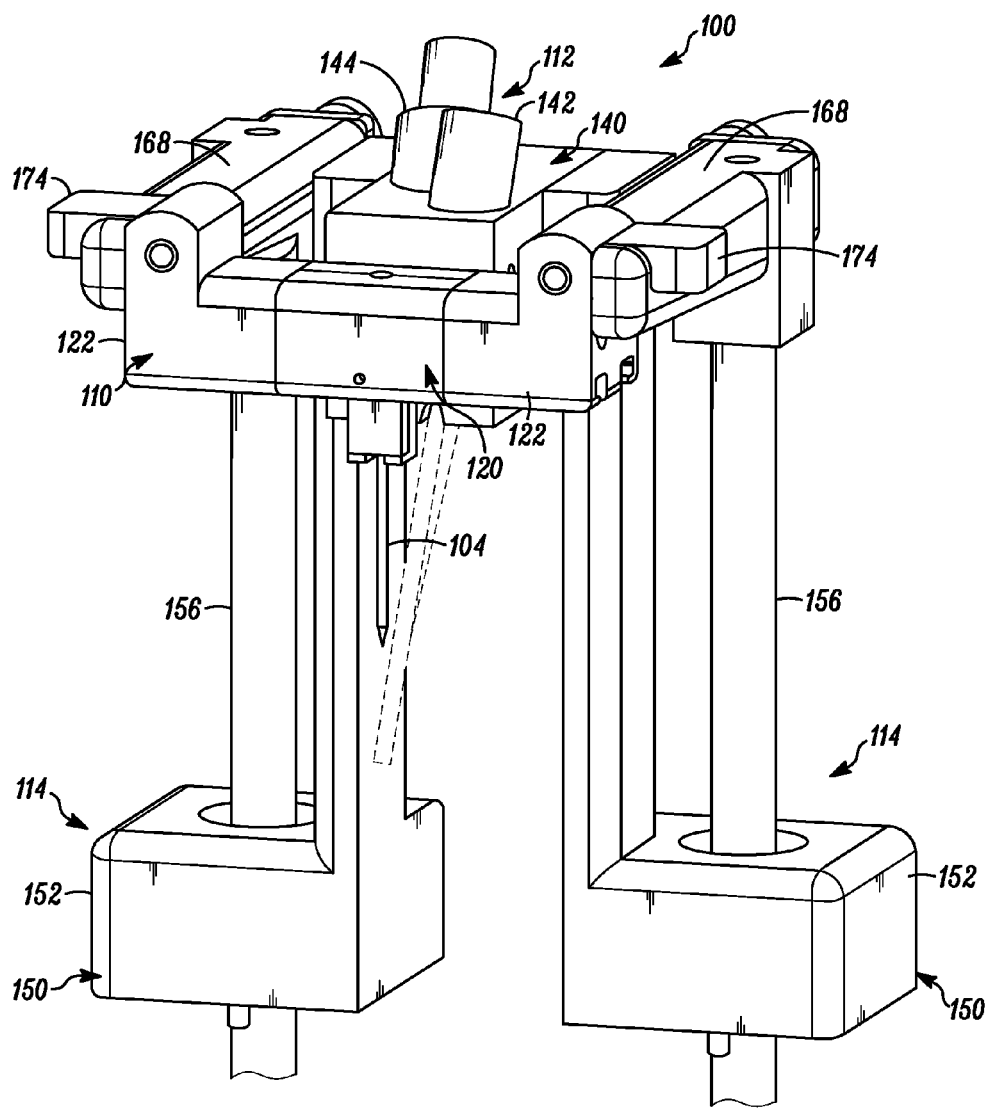
FIG. 5 is a perspective view of the assembly of FIG. 1, without the vial or container.
Figure 6:
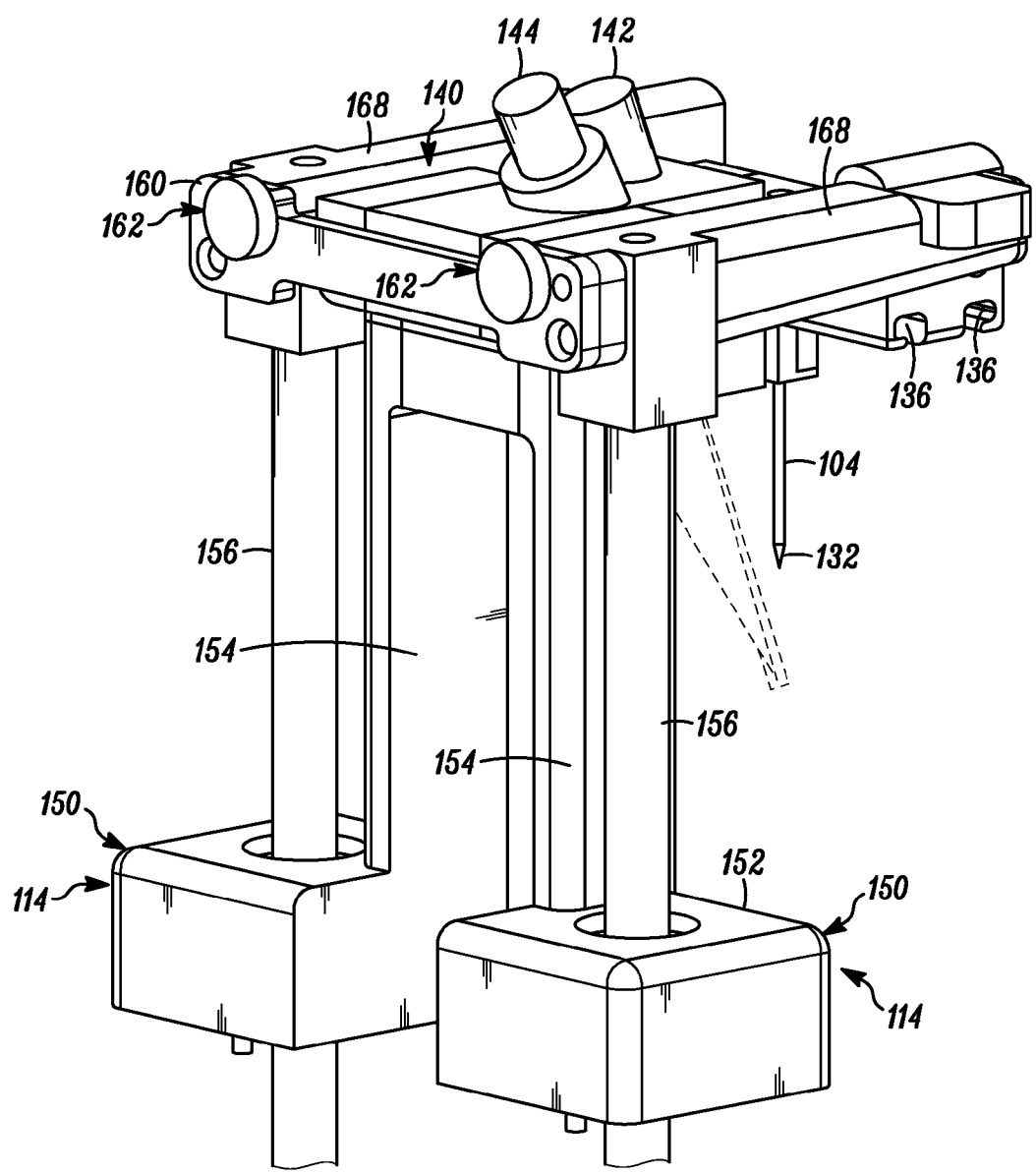
FIG. 6 is another perspective view of the assembly of FIG. 1.
Figure 7:
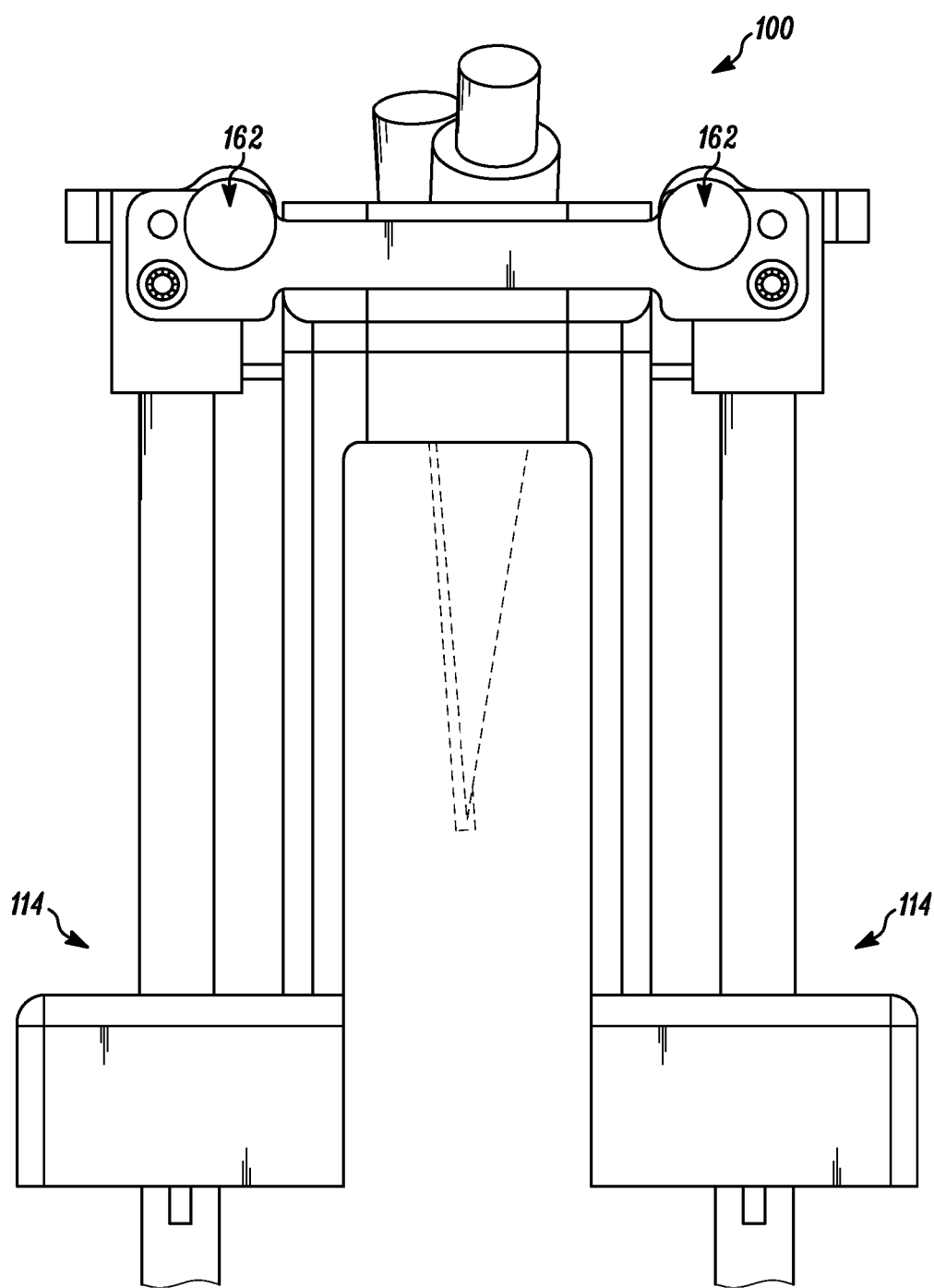
FIG. 7 is a back elevational view of the assembly of FIG. 1.
Figure 8:
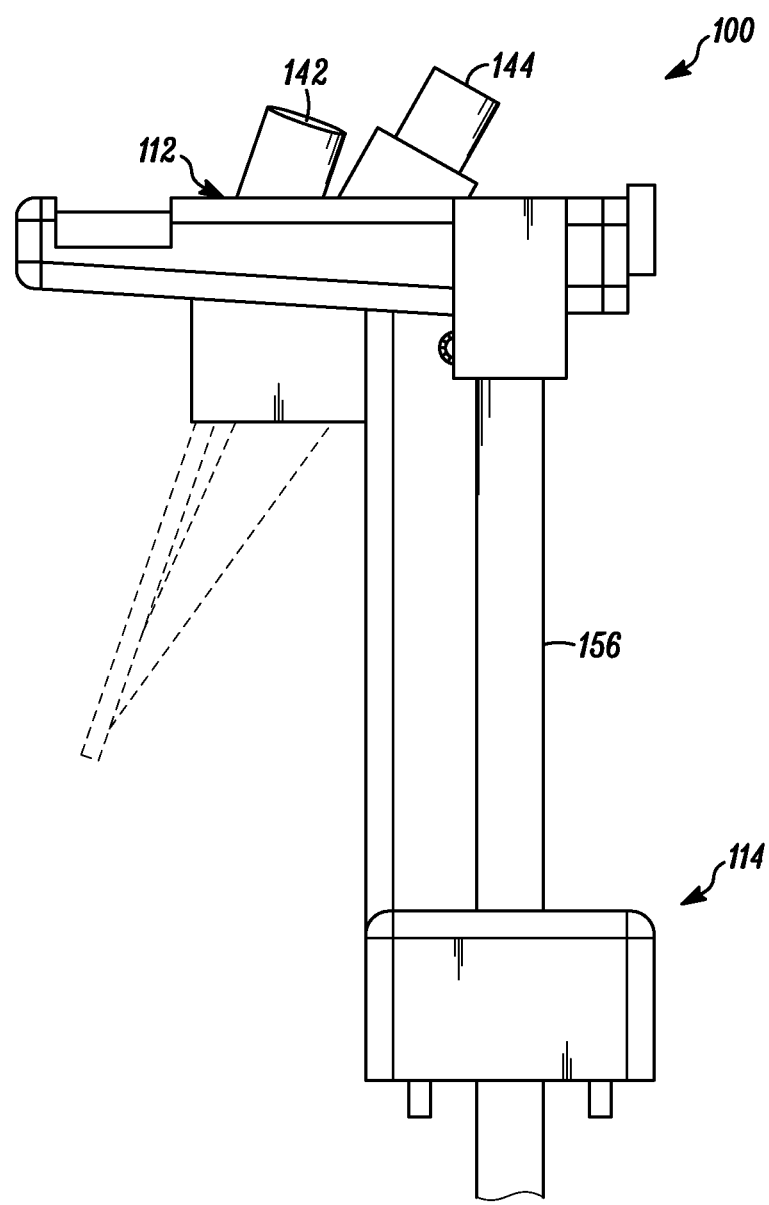
FIG. 8 is a side elevational view of the assembly of FIG. 1, with the needle manifold removed therefrom.
Figure 9:
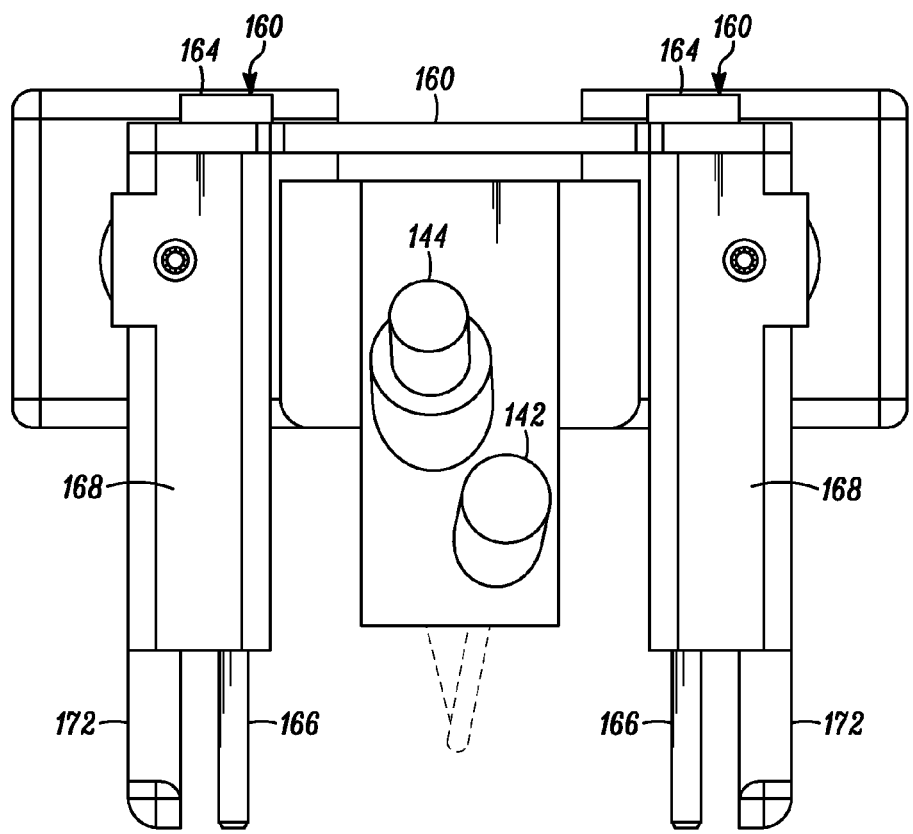
FIG. 9 is a top elevational view of the assembly of FIG. 1 with the needle manifold removed therefrom.
Figure 10:
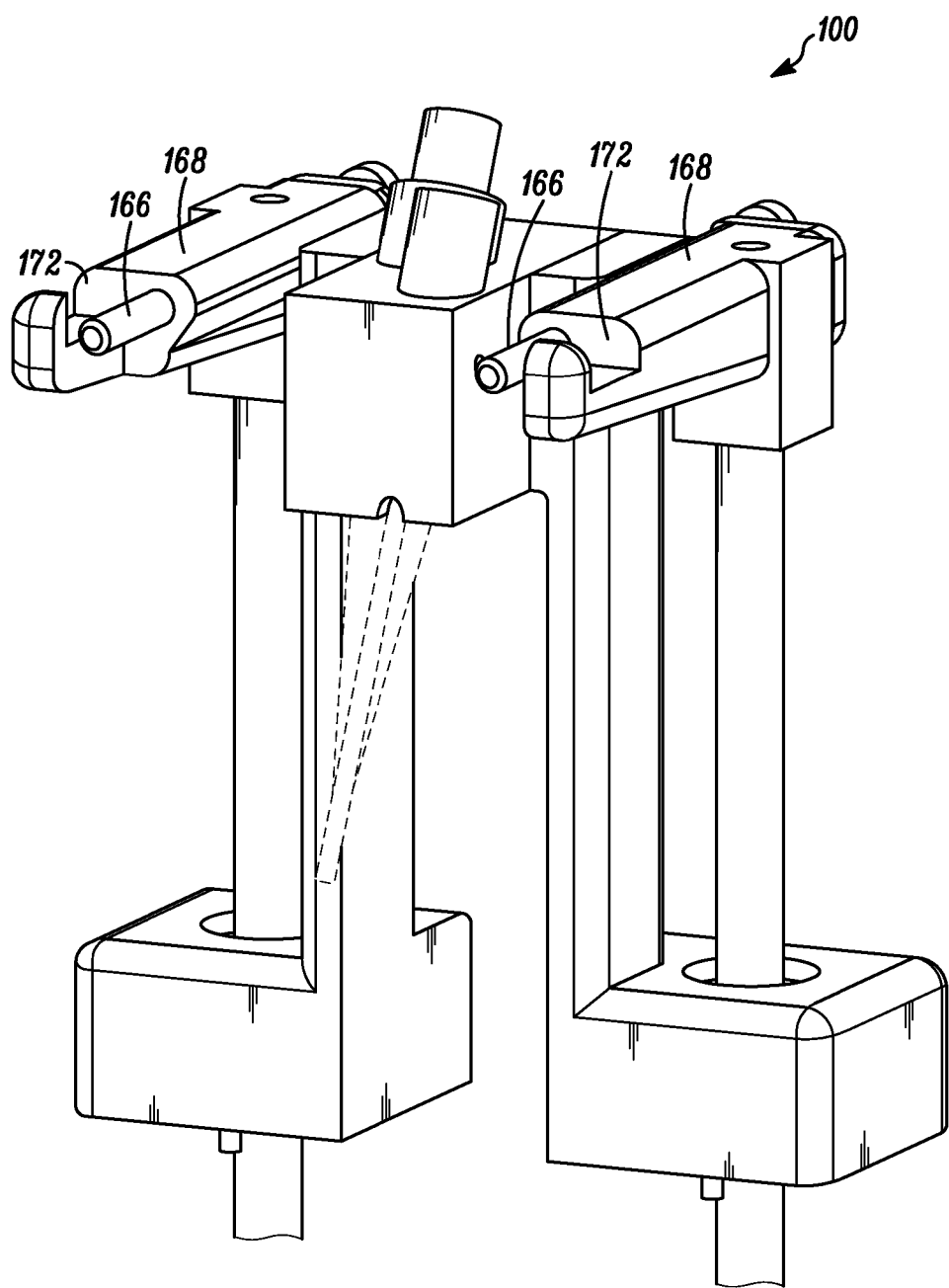
FIG. 10 is a perspective view of the assembly of FIG. 1 with the needle manifold removed therefrom.
Figure 11:
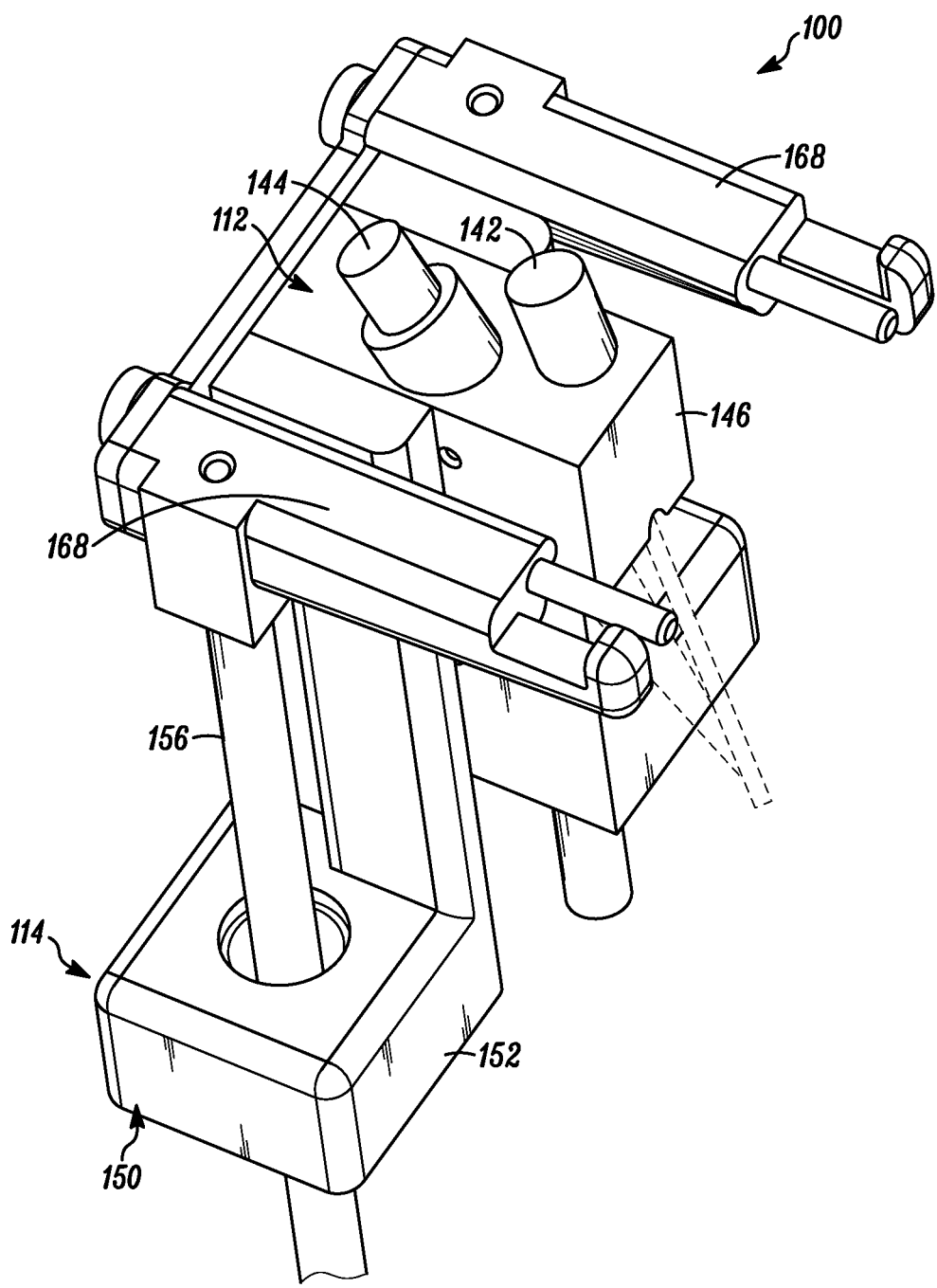
FIG. 11 is a perspective view of the assembly of FIG. 1 with the needle manifold removed therefrom.

Referring to FIGS. 1-7, an assembly 100 is illustrated. The assembly 100 is used in filling a vial 102 or other container with medicaments or other substances by temporary introduction of a needle 104 or syringe through a resealable cap or stopper 106 and sealing such vials or containers after such filling. The assembly 100 may be used, for example, in association with a conveyor system(s) that transports the vials or containers to/from the assembly and/or an enclosure to help prevent contaminants from reaching the assembly and/or vials or containers.

In addition, the assembly and/or methods described herein may be used, for example, in apparatus and/or methods disclosed in U.S. Pat. No. 6,604,561, which issued Aug. 12, 2003 entitled, "MEDICAMENT VIAL HAVING A HEAT-SEALABLE CAP, AND APPARATUS AND METHOD FOR FILLING THE VIAL", U.S. patent application Ser. No. 10/655,455, filed Sep. 3, 2003 entitled, "SEALED CONTAINERS AND METHODS OF MAKING AND FILLING SAME", U.S. patent application Ser. No. 10/766,172, filed on Jan. 28, 2004 entitled, "MEDICAMENT VIAL HAVING A HEAT-SEALABLE CAP, AND APPARATUS AND METHOD FOR FILLING THE VIAL", U.S. patent application Ser. No. 10/600,525, filed Jun. 19, 2003 entitled, "STERILE FILLING MACHINE HAVING NEEDLE FILLING STATION WITHIN E-BEAM CHAMBER", and U.S. patent application Ser. No. 60/550,805, filed Mar. 5, 2004 entitled, "APPARATUS FOR NEEDLE FILLING AND LASER RESEALING, each of which is hereby expressly incorporated by reference as part of the present disclosure. The assembly and/or methods described herein may also use one or more portions of the apparatus and/or methods disclosed in one or more of such applications. Furthermore, it should be recognized that one or more portions of the assembly and/or methods described herein may be used in association with one or more portions of the apparatus and/or methods disclosed in such applications.

The assembly 100 includes a first structure, which is referred to hereinafter as the needle manifold 110, and a support and drive assembly 114. The assembly 100 may also include a second structure, which is referred to hereinafter as the seal and sense unit manifold 112. The seal and sense unit manifold 112 is utilized if the user desires to seal the needle penetration area and sense that the seal is proper in the same assembly. Note that schematic representations of a laser beam 116 provided by the seal and sense unit manifold 112 and radiation 118 sensed by the seal and sense unit are also shown as dashed lines throughout the drawings.

Figure 28:
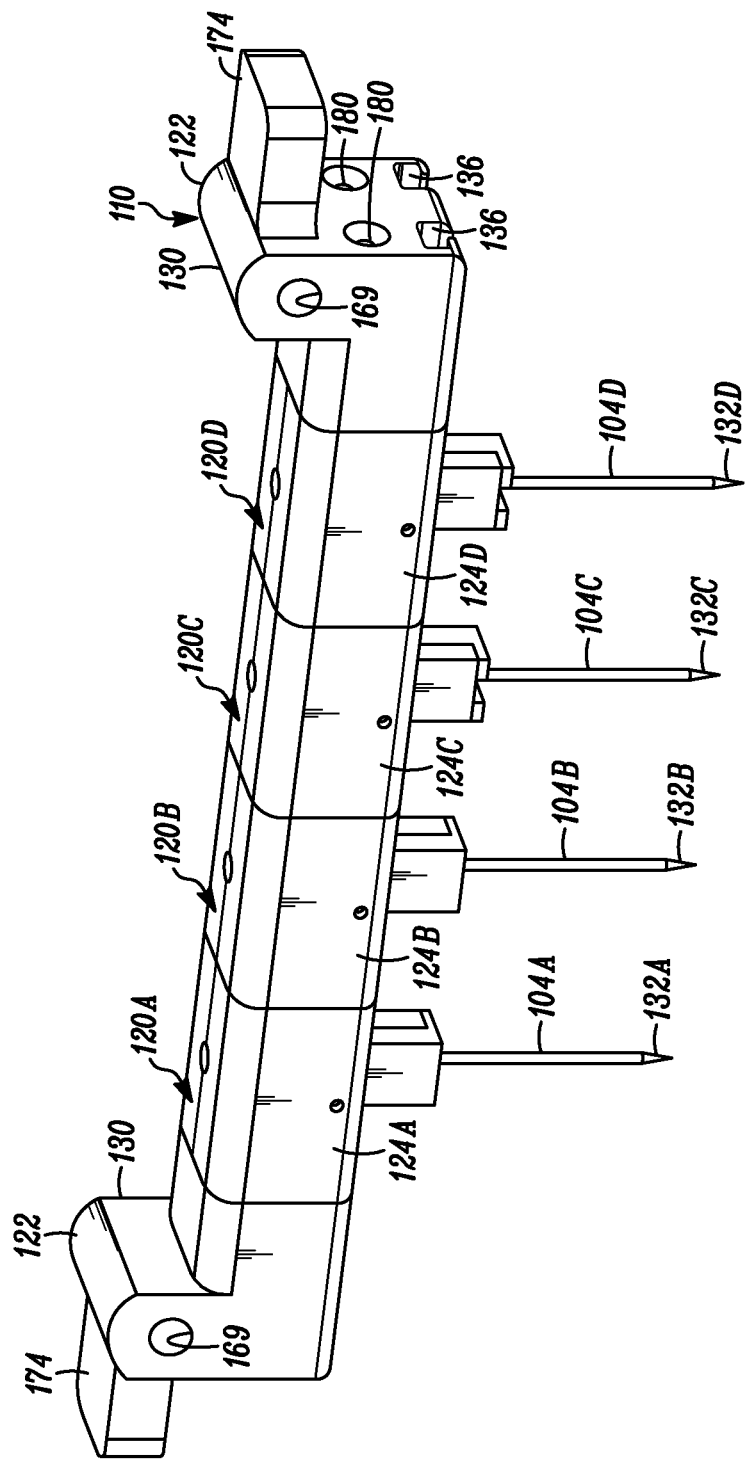
FIG. 28 is a side elevational view of the needle manifold after adjustment and addition of three additional needle assemblies.

The needle manifold 110 includes one or more needle assemblies 120 (only one being shown in FIG. 1) and one or more support assemblies 122. As shown in FIG. 28, if more than one needle assembly 120 is employed, the needle assemblies (shown as 120A, 120B, 120C, and 120D) are, for example, arranged linearly and adjacent to one another (side by side) at respective positions in the manifold 110. Each needle assembly 120 includes the needle 104 and a needle support 124. The needles 104 are used to deliver medicament or other substance(s) into vials or other containers. In order to accommodate multiple needle assemblies 120, the needle manifold 110 is adjustable in that needle assemblies 120 can be added to and/or removed from the manifold 110 in order to provide a specific number of needles 104 desired in a particular application.

Referring again to FIGS. 1-7, each of the needles 104 has a port in flow communication with one or more sources of medicament or other substances (not shown). This flow communication may be provided, for example, by flexible tubes (not shown). Providing multiple needles makes it possible to fill multiple containers concurrently, if desired. As can be seen, each needle 104 is preferably a non-coring needle.

The support assemblies 122 are shown disposed at opposite ends of the needle manifold 110 on opposite sides of the needle assembly(s) 120. Each support assembly 122 includes a stopper portion 130. The needle manifold 110 is removable from the assembly, so as to enable the needle manifold 110 to undergo maintenance, cleaning, sterilization, and/or repair or replacement. FIGS. 8-11 illustrate the assembly 100 with the needle manifold removed. As will be further described below, the needle manifold 110 and the support and drive assembly 114 are provided with complementary catches that engage one another to releasably retain the needle manifold 110 to the support and drive assembly 114.

Figure 27:
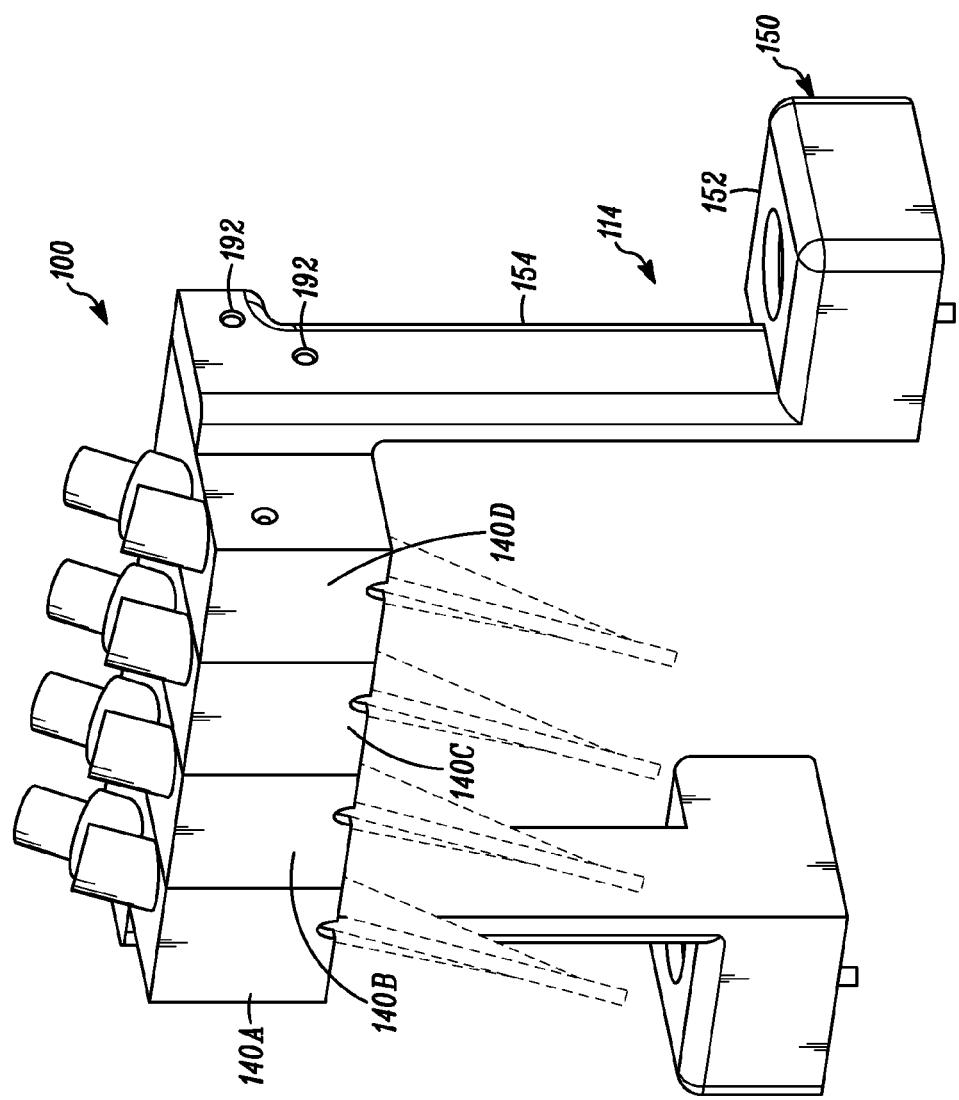
FIG. 27 is a perspective view of the assembly of FIG. 26.

The seal and sense unit manifold 112 includes one or more seal and sense assemblies 140 (only one being shown in FIG. 1). As shown in FIGS. 26 and 27, if the manifold 112 has more than one assembly 140, the seal and sense assemblies (shown as 140A, 140B, 140C, and 140D) are, for example, arranged linearly and adjacent to one another at respective positions in the seal and sense unit manifold 112. Each seal and sense assembly 140 may include, for example, a laser optic source assembly 142, an infrared ("IR") sensor 144, and a support portion 146. Each laser optic assembly 142 is adapted to provide the laser beam 116 to reseal a resealable cap or stopper 106 on the vial 102 after the vial 102 has been filled by needle 104. It is understood that the needle 104 penetrates the stopper 106 in order to fill the vial 102. The laser beam reseals the penetration area on the stopper 106. Each of the laser optic assemblies 142 may include a laser source or may be connected, for example, to a respective fiber optic cable (not shown) that connects the respective laser optic assembly to a respective laser source. Providing multiple laser optic assemblies 142 makes it possible to reseal multiple vials or containers concurrently.

While the seal and sense manifold 112 (or second structure) and the seal and sense assembly 140 are discussed throughout this application as being one unit, it is understood the seal assembly and the sense assembly may be two separate units and that the manifold 112 may include only one of those assemblies. In addition, assembly 100 may have only a seal assembly, which would seal the penetration area created by the needle. In an exemplary embodiment, the seal assembly is the laser optic source assembly 142 and the sense assembly is the IR sensors 144, which are illustrated in the figures.

The IR sensors 144 may be used, for example, to detect the temperature of the needle penetration region during resealing, and therefore can be used to determine whether the cap or stopper 106 (FIG. 1) was sufficiently reheated to achieve resealing. Each of the IR sensors 144 includes, or is connected to, a respective IR sensor module (not shown). Providing multiple IR sensors 144 enables sensing the temperature of multiple vials or containers concurrently, for example, as they are being resealed or immediately thereafter.

As with the needle manifold 110 (FIG. 28), the sealing and sensing unit manifold 112 is adjustable in that sealing and sensing assemblies 140 can be added to, and/or removed from, the manifold in order to provide a specific number of sealing and sensing assemblies desired in a particular application. In some embodiments, the manifold 112 also may be provided with a removable cover to protect the assemblies, e.g., during transport.

Referring to FIGS. 1-11, the support and drive assembly 114 is adapted to drivingly support the needle manifold 110 and also to support the seal and sense manifold 112. This assembly 114 may include, for example, a pair of generally L-shaped stands 150, each having a base 152 and support column 154 extending therefrom. Each base has a drive shaft 156 extending therefrom, that is drivingly connected to a drive unit, e.g., a stepper motor (not shown) that has a lead screw drivingly coupled to a base plate (not shown) and is mounted, for example, within the base or beneath a base plate (not shown) supporting the assembly 100.

The support and drive assembly 114 further includes a brace 160 fixedly secured at opposite ends to a pair of laterally-extending support arms 168. Each support arm 168 is fixedly secured to the upper end of a respective drive shaft 156 and is vertically movable therewith. The assembly 114 further includes a pair of thumb screws 162, and each thumb screw includes a head portion 164 and a rod portion 166. Each rod portion 166 extends through one end of the brace 160 and respective support arm 168. The free end of each rod portion 166, which is the opposite end from thumb screw 162, threadedly engages a respective threaded hole 169 formed in a respective support 130 of the needle manifold 110 to releasably retain the needle manifold 110 to the support and drive assembly 114. It should be understood that other types of releasable connectors may be employed, including but not limited to, fasteners (e.g., bolts), clamps, etc.

Referring to FIGS. 1-11 and 18-21, each support arm 168 defines on its free end an approximately u-shaped recess 172 for receiving therein a complementary shaped, laterally-extending flange 174 formed on the respective support portion 130 of the needle manifold 110. Thus, in order to assemble the needle manifold 110 to the support arms 168, the user grips the laterally-extending flanges 174 of the manifold 110 and lowers the flanges into the respective u-shaped recesses 172 of the support arms. Then, the user pushes the thumb screws 162 forwardly such that the threaded ends of the rod portions 166 are received within the respective threaded holes 169 of the support portions 130. The user then simply turns the head portions 164 of the thumb screws to fixedly secure the manifold to the support arms.

One advantage of the illustrated embodiment of the present invention is that the user may be located on the opposite side of the station 100 relative to the vials or containers 102 (or the location for filling and/or re-sealing the containers). In addition, since the user need only grip the laterally-extending flanges 174 of the needle manifold 120 to install the manifold, the user's hands will not extend over the location at which the vials or other containers are filled and/or resealed (i.e., the user need not break the needle plane), but rather will be located to the sides of this area. Accordingly, this design further prevents the possibility that the needle filling and/or laser re-sealing location might become contaminated during removal or installation of the needle manifold.

Another advantage of the illustrated embodiment is that the needle filling and laser sealing station 100 can be mounted within a sterile enclosure that includes glove ports for allowing an operator's hands to access the interior of the enclosure therethrough. Further, a user can easily remove and install the needle manifold by employing such glove ports or other means for accessing the interior of a sterile enclosure. As indicated above, the user need only manipulate the thumb screws to remove and install the needle manifold.

In addition, the filling, sealing and sensing assembly 100 may be provided with laminar flow 170 (FIG. 2) as part of the overall system for helping reduce the possibility of contamination. In this embodiment, the laminar airflow is substantially horizontal or substantially parallel to the base plate of the assembly.

Figure 12:
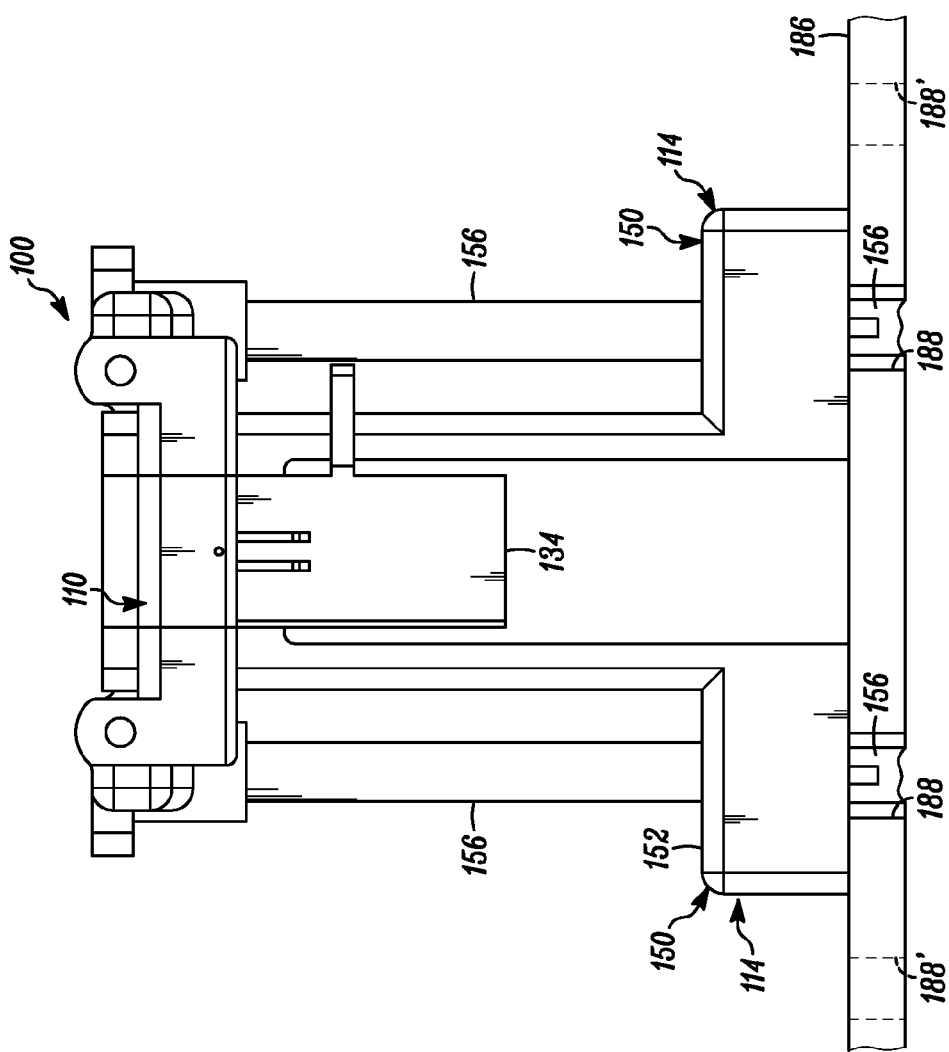
FIG. 12 is a front elevational view of the assembly of FIG. 1 and a cover installed on the needle manifold.
Figure 13:
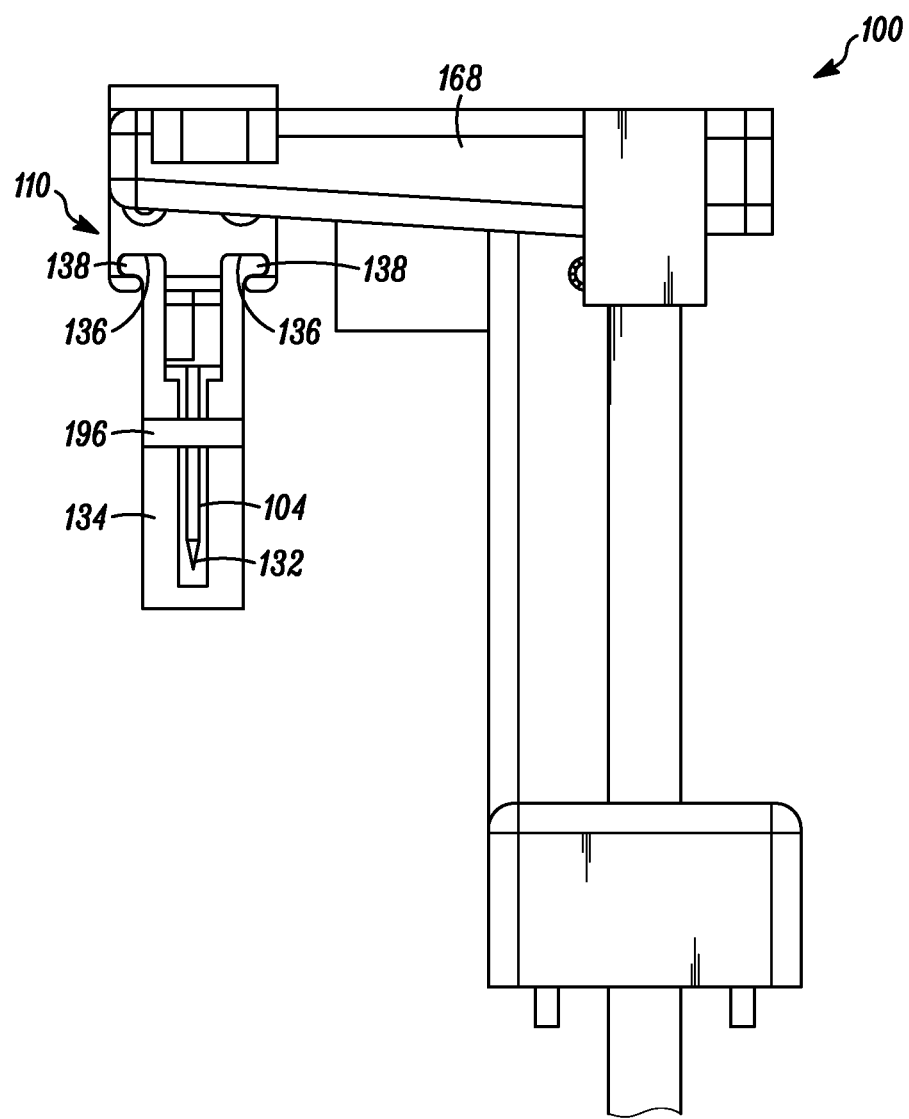
FIG. 13 is a side elevational view of the assembly of FIG. 1 and a cover installed on the needle manifold.
Figure 14:
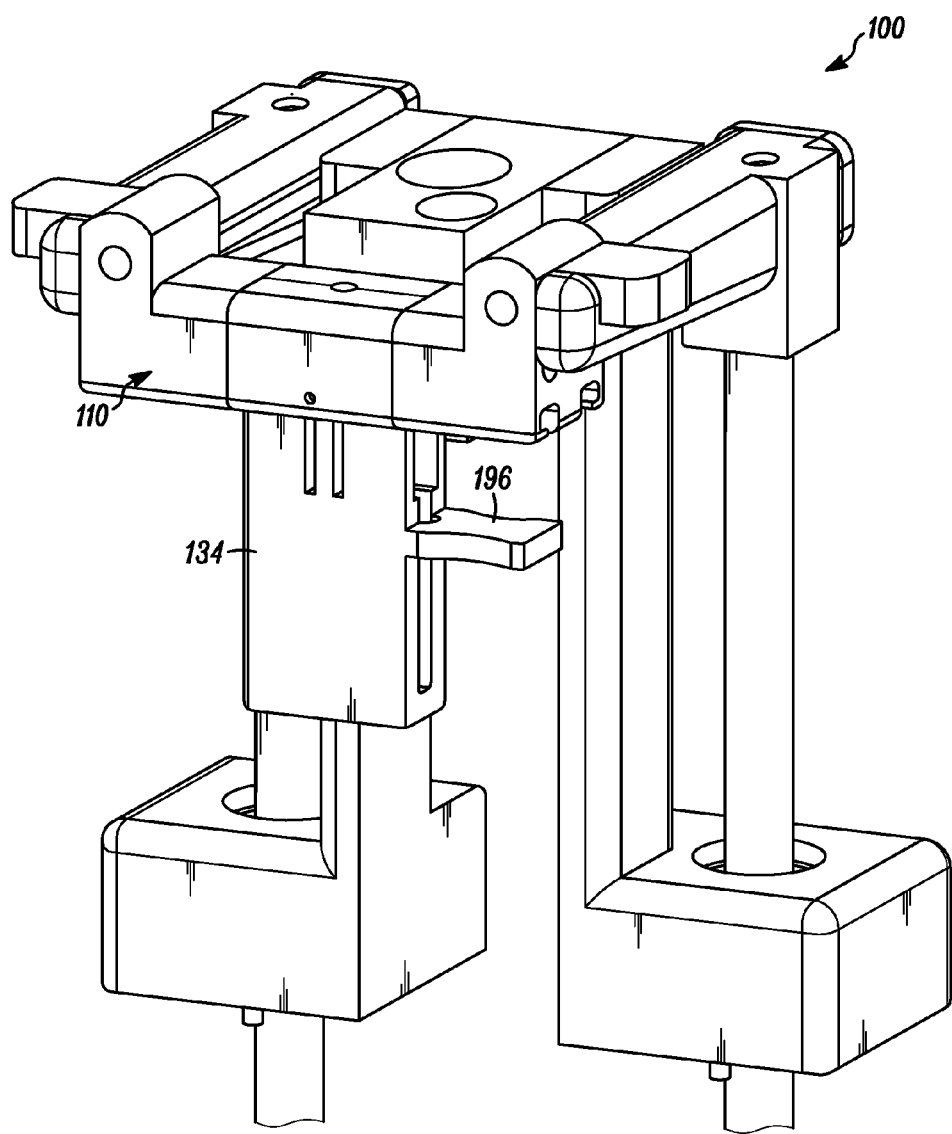
FIG. 14 is a perspective view of the assembly of FIG. 1 and the cover of FIG. 13.
Figure 15:
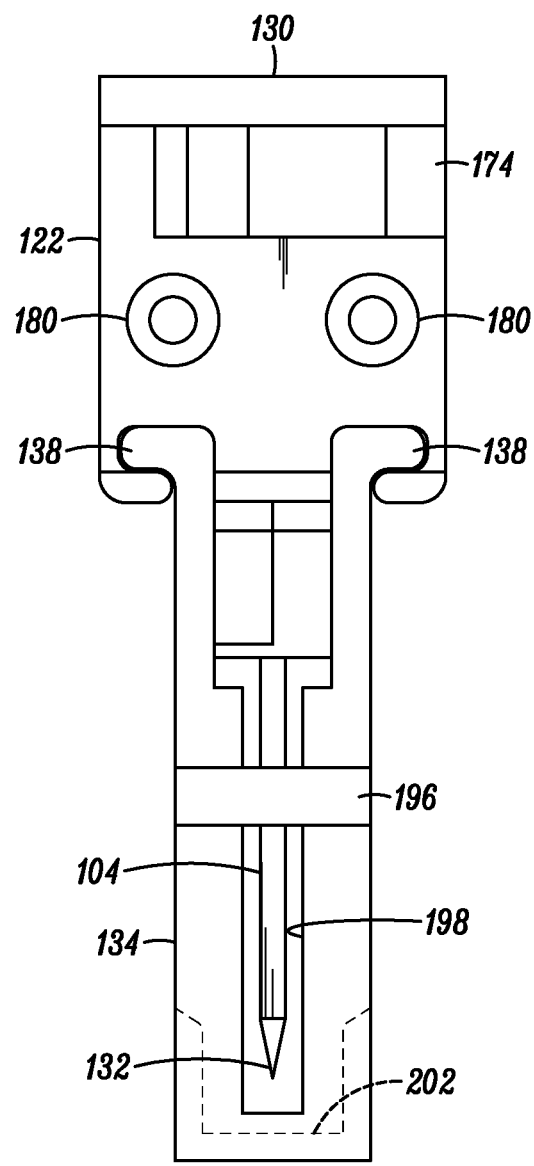
FIG. 15 is a side elevational view of the needle manifold with a cover removably connected thereto.
Figure 16:
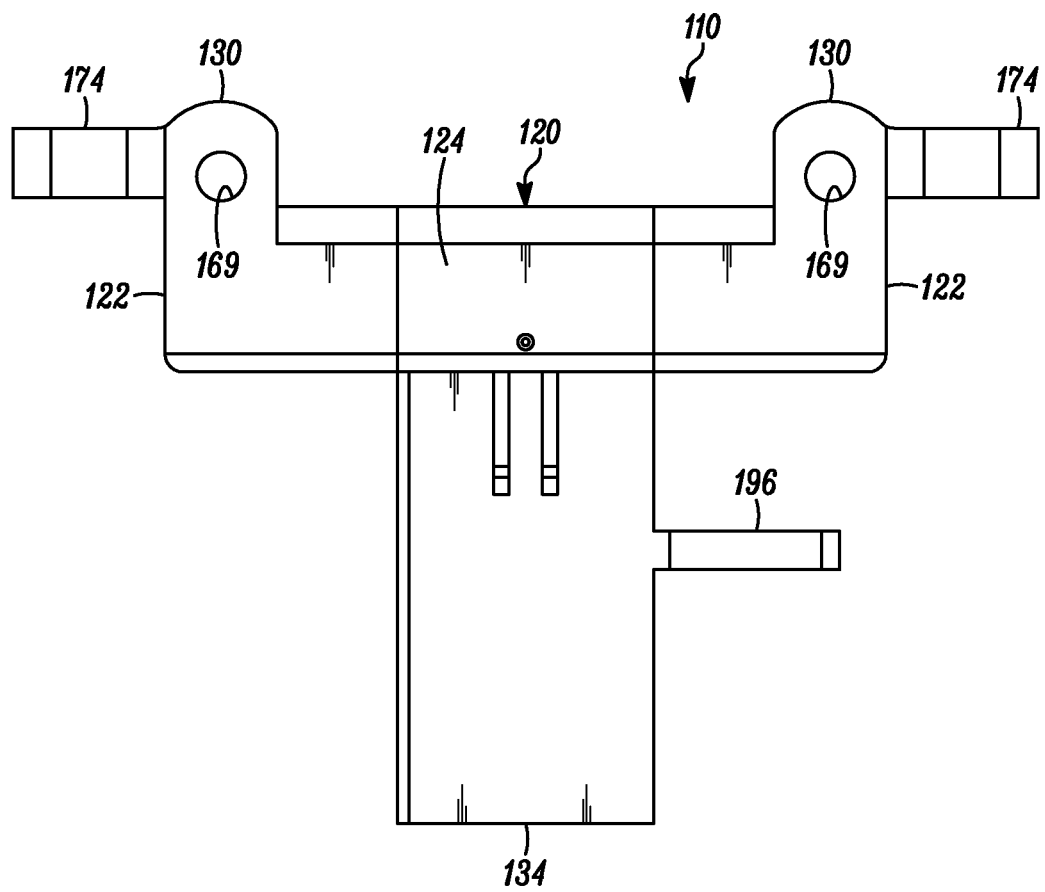
FIG. 16 is a side elevational view of the needle manifold with the cover.
Figure 17:
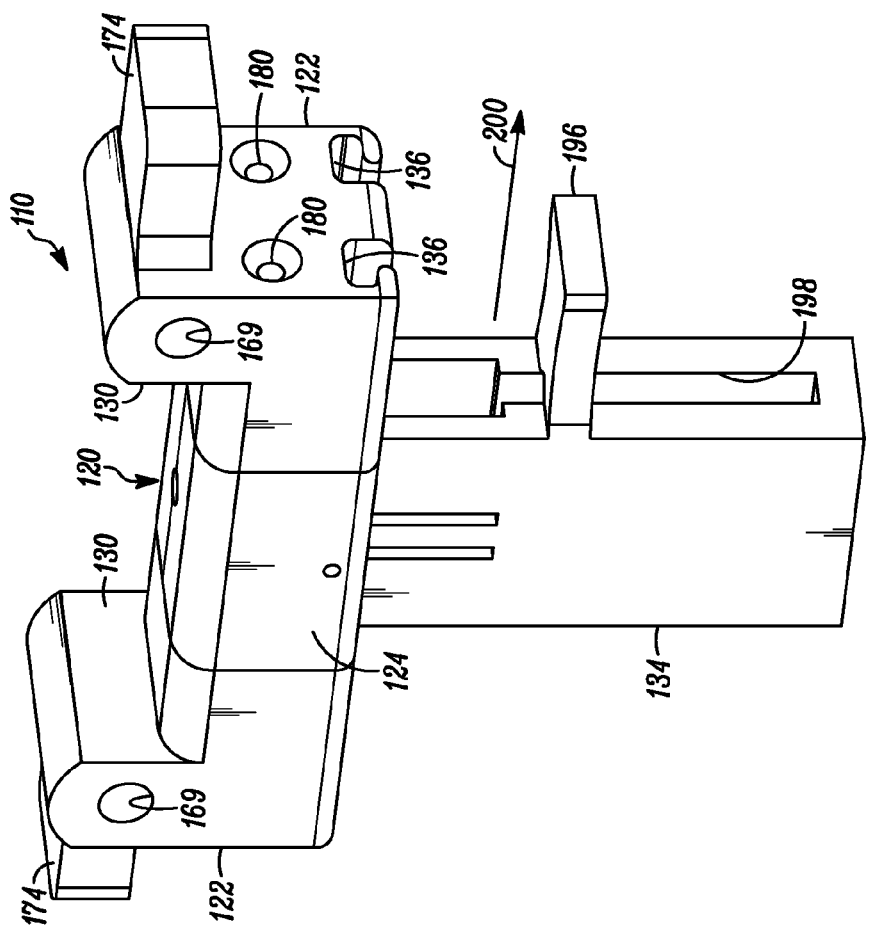
FIG. 17 is a perspective view of the needle manifold with the cover.
Figure 18:
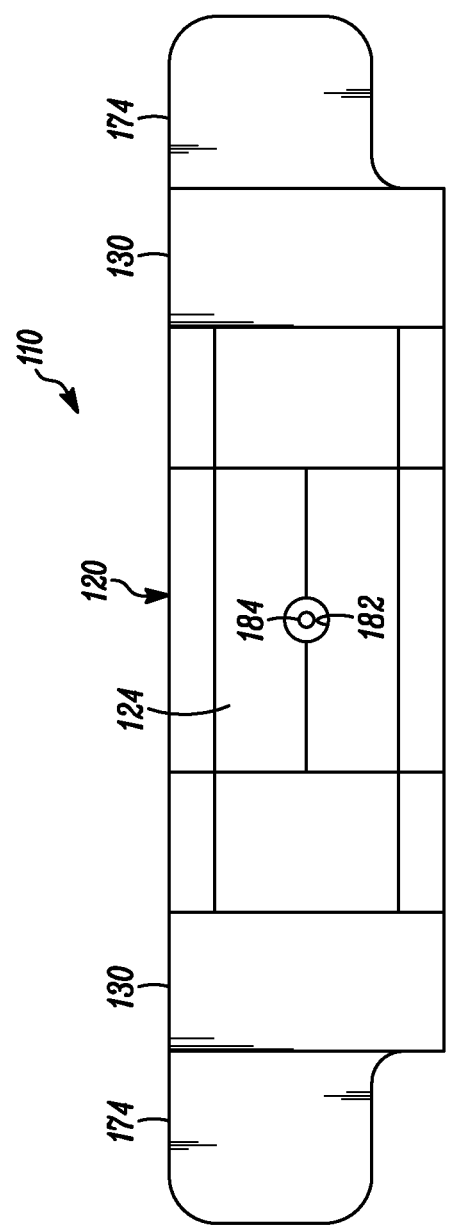
FIG. 18 is a top elevational view of the needle manifold.
Figure 19:
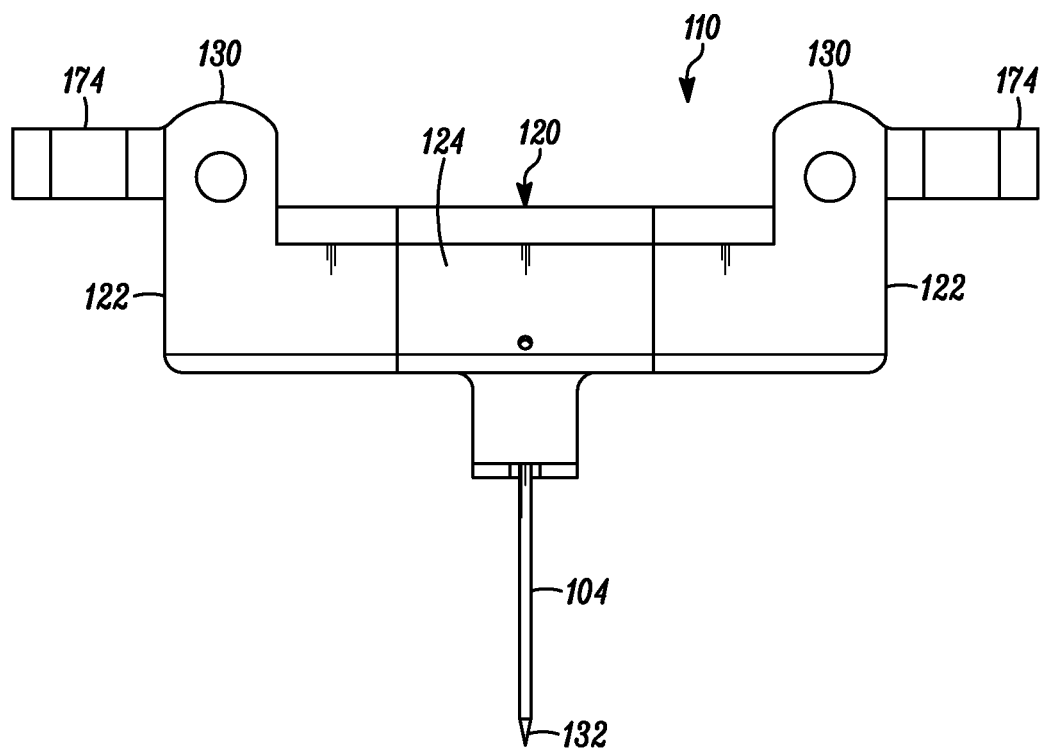
FIG. 19 is a side elevational view of the needle manifold without the cover.
Figure 20:
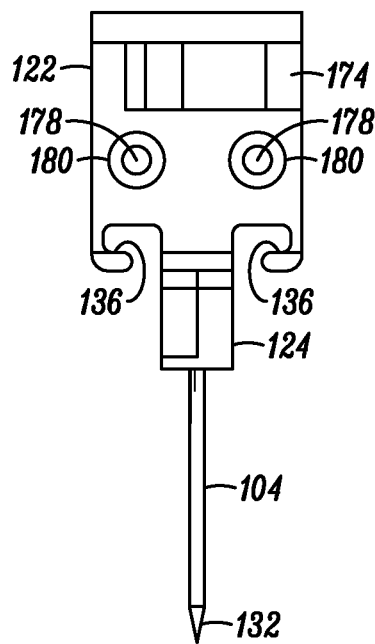
FIG. 20 is a side elevational view of the needle manifold.
Figure 21:
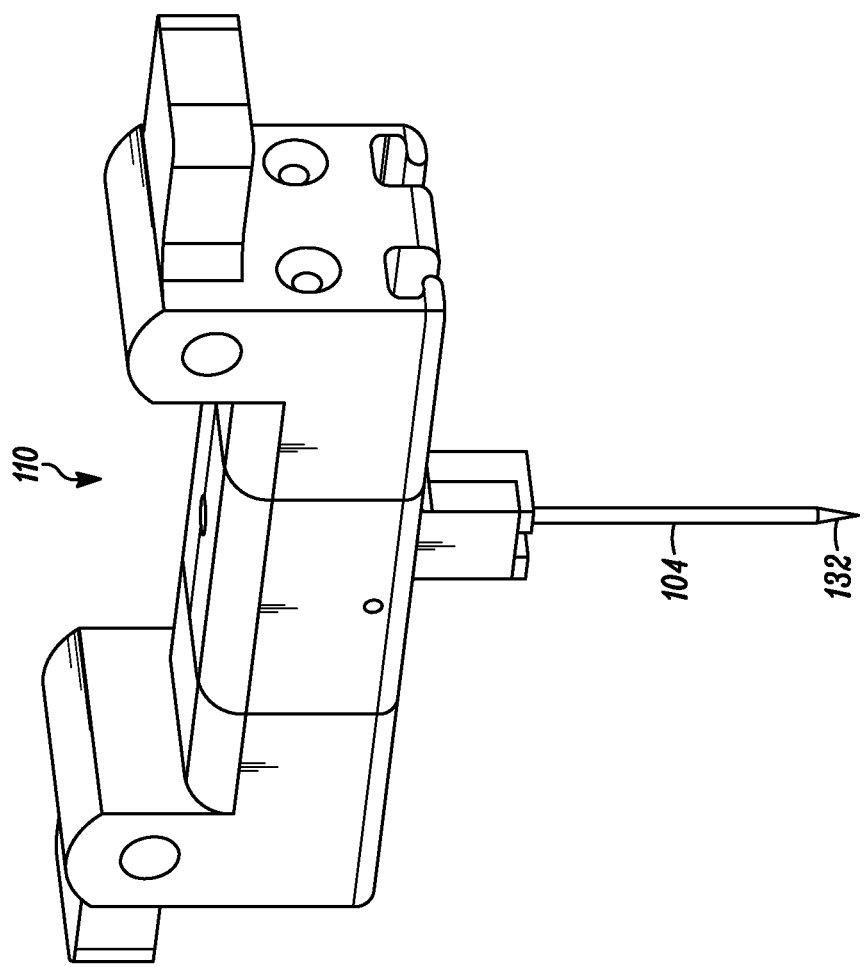
FIG. 21 is a perspective view of the needle manifold.

Referring FIGS. 12-14, needle 104 is illustrated with a cover 134. Because the needles 104 preferably define non-coring, sharp tips 132 that are capable of causing injury and/or becoming damaged during removal, transport, or installation of the manifold onto, or off of the assembly, the manifold 110 may be adapted to receive the cover 134 that limits or prevents access to the needles during certain times. As will be further described below, the manifold 110 and cover 134 each may be provided with complementary catches that engage one another to releasably retain the cover to the manifold. In this embodiment, for example, the needle manifold 110 defines one or more grooves 136, and the cover 134 defines one or more flanges 138 that are removably received by the groove(s) to retain the cover to the manifold at desired times.

Referring to FIGS. 12-17, the cover 134 includes a laterally-extending handle 196 that extends approximately perpendicular to the axis or axes of the needle(s) 104. The cover 134 further defines an elongated slot 198 extending from one end of the cover to the other for receiving within the housing the needles 104. As indicated by the arrow 200, the cover 134 is removed by gripping the handle 196 and pulling the cover laterally in the direction of the arrow 200.

In doing so, the flanges 138 of the cover 134 slidably move through the grooves 136 of the manifold until the cover is released therefrom. The open end of the cover defined by the slot 198 located opposite the handle 196 allows the cover to be slipped away from the needles.

One of the advantages of the cover 134 is that it allows a user to safely handle the needle manifold during sterilization, installation and/or removal. Preferably, the cover and components of the needle manifold are made of suitable materials to allow gamma or other sterilization thereof prior to installation in the station 100. If desired, and as indicated in broken lines in FIG. 18, the base of the slot 198 may define a recess or receptacle 202 for receiving fluid, such as the medicament or other substance to be pumped through the needles 104 and into the containers. After the needle manifold 110 is installed, and the fill tubes (not shown) are connected to the inlets 184 of the needles 104, it is typically necessary to purge any air from the fill tubes and needles prior to filling the vials or other containers. During the purging process, it may be necessary to release the medicament or other substance through the needles to ensure that the needles and lines connected thereto are substantially airless. The cover 134 and receptacle 202 thereof may be used during the purging process to collect any such fluid or other substance released from the needles. Then, the cover may be removed and the collected fluid or other substance discarded.

Referring to FIG. 12, the support and drive assembly 114 may be mounted on a base plate or other support 186 defining laterally-spaced apertures 188 for receiving therethrough the drives shafts 156. As indicated in broken lines, the support 188 may define any desired number of additional apertures 188' to accommodate different configurations of the needle manifold, and thereby allow the stands 150 to be located where necessary to accommodate the different configurations of the needle manifold. Alternatively, the support 186 may define one or more elongated slots rather than discrete apertures 188 to thereby allow the shafts to be moved laterally therethrough to accommodate the different needle manifold configurations.

Figure 23:
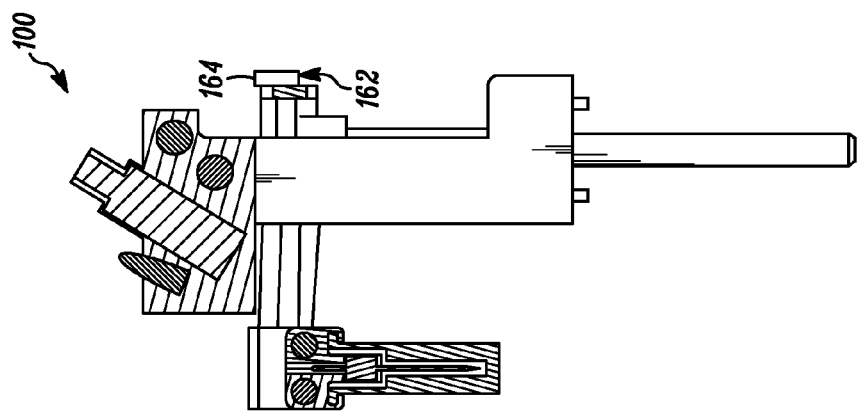
FIG. 23 is a cross-sectional view of the needle assembly of FIG. 22 along line 30-30.
Figure 22:
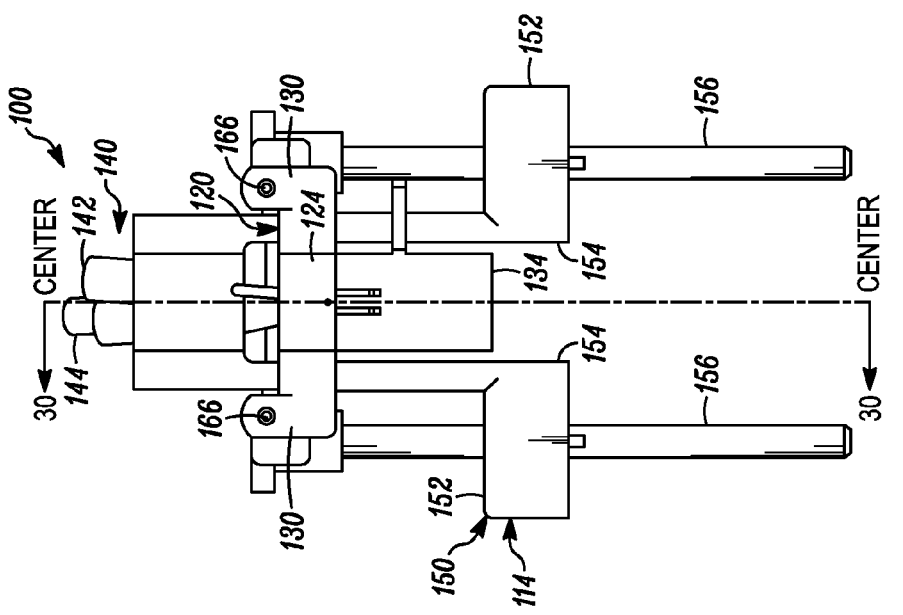
FIG. 22 is an elevational view of a needle assembly of FIG. 1.

Referring to FIGS. 22 and 23, the support 124 of each needle assembly 120 defines a pair of substantially parallel apertures 176 extending through the support and oriented approximately perpendicular to the axis of the respective needle 104. A pair of needle shafts 178 is received through the respective apertures 176 and extends outwardly on opposite sides of the support 124. As shown typically in FIG. 20, the ends of the shafts 178 are press fit or otherwise fixedly received within corresponding apertures 180 formed in the end supports 122 of the manifold to assemble the needle assembly 120 to the end supports 122. In the multi-needle assembly embodiment of FIG. 28, the shafts 178 (FIG. 23) are sufficiently long to mount the desired number of needle assemblies between the end supports 122 of the needle manifold.

Referring again to FIGS. 22 and 23, each needle support 124 defines opposing grooves 136, and each end support 122 likewise defines opposing grooves 136 that are aligned with the grooves of the needle assemblies to create continuous grooves 136 in the assembled needle manifold. The needle support 124 defines an aperture 182, and the input end 184 of the respective needle 104 extends into the aperture 182. The input end 184 of the needle 104 is spaced inwardly relative to the wall of the aperture 182 to allow an inlet tube (not shown) to be secured to the needle inlet and fit therebetween. If desired, the needle support 124 may be made of two parts 124A, 124B that are secured together by one or more fasteners (not shown) to clamp, or otherwise fixedly secure the respective needle 104 therebetween.

Another advantage of the illustrated embodiments of the present invention is that the number of needles 104 and/or needle assemblies 120 mounted on the needle manifold easily may be adjusted by simply adjusting the lengths of the needle shafts 178. Thus, a user may maintain any desired number of needle assemblies 120, and associated needle shafts 178 and braces 160, to accommodate the different desired manifold configurations.

Figure 25:
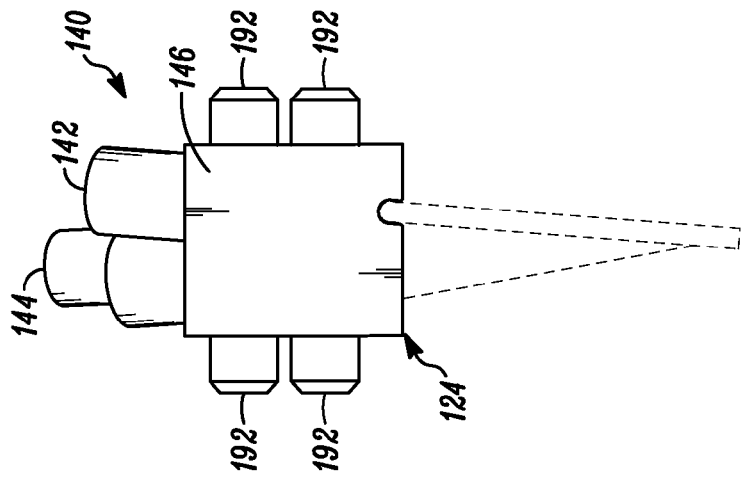
FIG. 25 is a front elevational view of the seal and sense assembly of FIG. 24.
Figure 24:
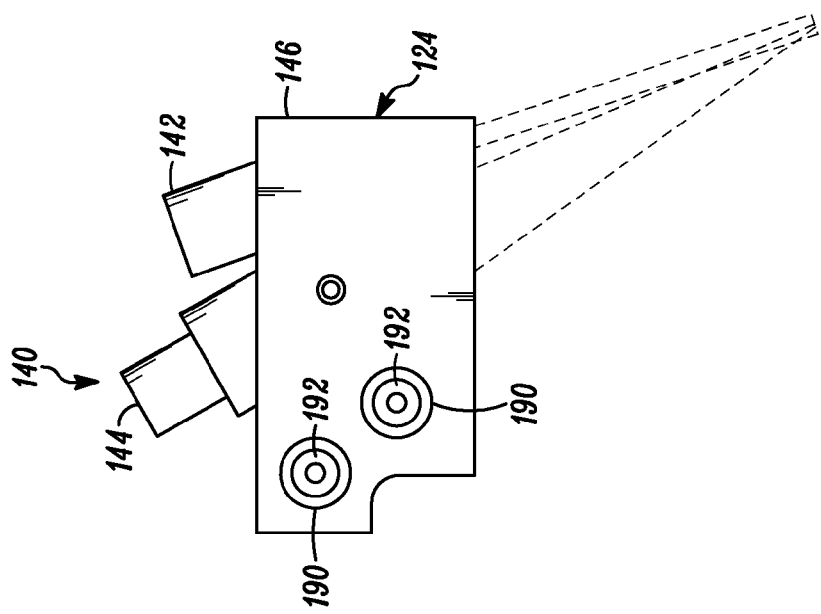
FIG. 24 is a side elevational view of a seal and sense assembly of the assembly of FIG. 1.

Referring to FIGS. 24 and 25, the support 124 of each seal and sense assembly 140 defines a pair of substantially parallel apertures 190 extending through the support and oriented approximately perpendicular to the axes of the drive shafts 156 (FIG. 1). A pair of mounting shafts 192 is received through the respective apertures 190 and extends outwardly on opposite sides of the support 146. The ends of the shafts 192 are press fit or otherwise fixedly received within corresponding apertures 194 formed in the end support columns 154 to assemble the seal and sense assembly to the columns. In the multi-sensor and multi-needle assembly embodiment of Referring to FIG. 27, the shafts 192 are sufficiently long to mount the desired number of seal and sense assemblies between the end columns 154.

Figure 29:
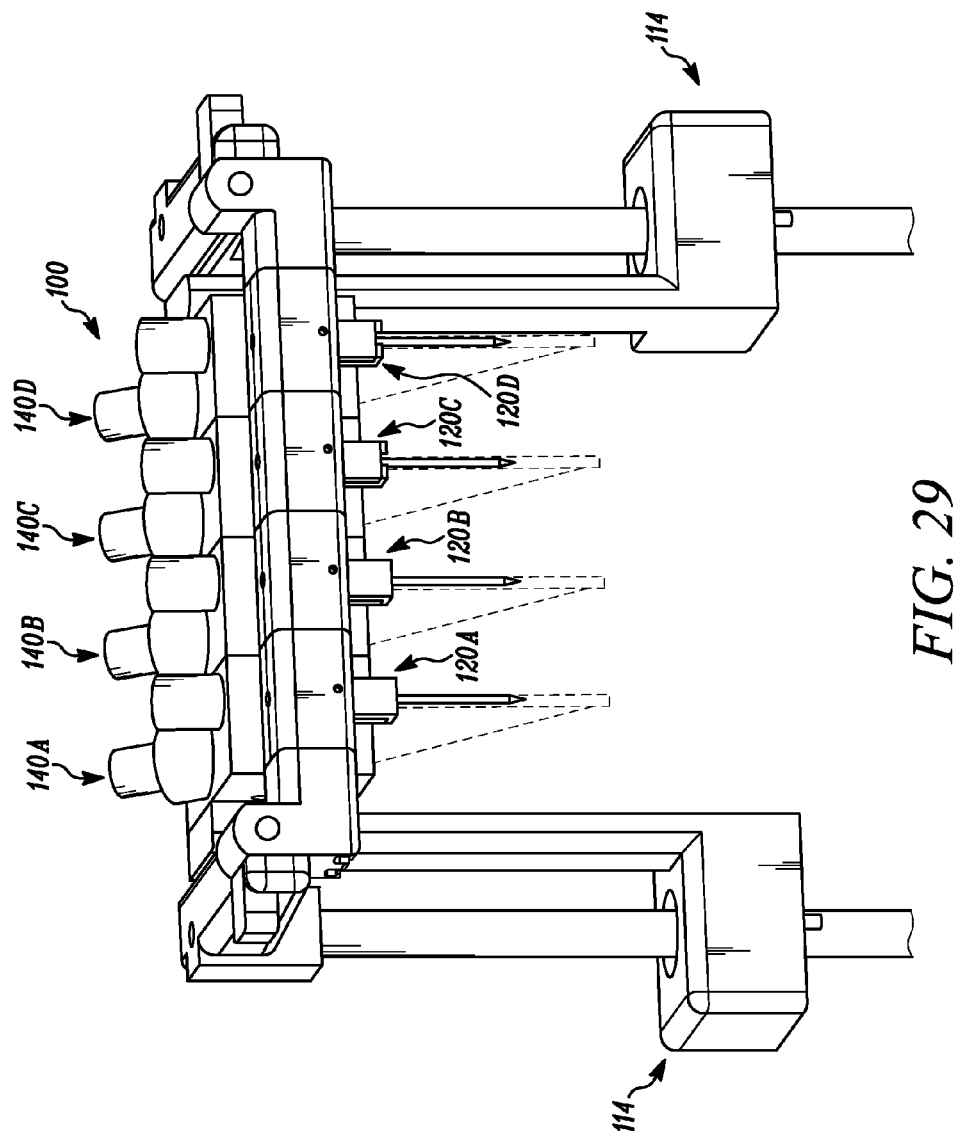
FIG. 29 is a perspective view of the assembly of FIG. 26 and the needle manifold as shown in FIG. 26.

Referring to FIGS. 29 and 30, another advantage of the illustrated embodiments of the present invention is that the user may include any desired number of seal and sense assemblies to accommodate any desired number of needle manifolds. Thus, a user may maintain, in addition to any desired number of needle manifolds, braces and needle shafts as described above, and an associated number of seal and sense assemblies and associated mounting shafts. Thus, the stations of the currently preferred embodiments of the present invention easily lend themselves to being adjusted by users in the manner indicated, or alternatively, to being manufactured in different single or multi-needle, and/or single or multi-sense and seal assembly, configurations.

Although each needle assembly 120 shown above has only one needle, the needle assemblies are not limited to one needle. For example, in some other embodiments, one or more of the needle assemblies 120 may have two or more needles. Although the needle assemblies 120 are shown arranged linearly and adjacent one another, this is not required. The support assemblies 122 need not be disposed at the ends of the needle manifold. For example, in some embodiments, one or more support assemblies may be disposed between one or more needle assemblies.

It should be understood that the needle manifold 110 may be used without the sealing and sensing manifold 112. Thus, one aspect of the present disclosure is an apparatus for use in association with a filling station, where the apparatus comprises a manifold having two stoppers, spaced apart from one another, for capturing at least one needle assembly therebetween, at least one of the stoppers being movable relative to the other to change the size of the spacing therebetween to allow a change in the number of needle assemblies captured therebetween.

Similarly, the sealing and sensing manifold may be used without the needle manifold. Moreover, it should be understood that the sealing or sensing portion of the sealing and sensing manifold may be employed without the other, to provide a sealing manifold and/or a sensing manifold. Alternatively, the sealing and sensing manifold may be located downstream of the needle manifold.

In addition, it should be understood that an adjustable needle manifold may be employed without a cover. Further, it should also be understood that the cover may be employed on a non-adjustable manifold.

Thus, while there have been shown and described various embodiments, it will be understood by those skilled in the art that the present invention is not limited to such embodiments, which have been presented by way of example only, and that various changes and modifications may be made without departing from the spirit and scope of the invention.

What is claimed is:

1. A method comprising:
   determining a number of containers that are to be filled concurrently; and
   adjusting an adjustable assembly, which is adjustable to receive one or more filling assemblies and one or more seal assemblies, to include at least one of said filling assemblies and at least one of said seal assemblies such that a number of said filling assemblies and said seal assemblies equals said number of containers.

2. The method of claim 1, further comprising feeding said number of containers into said adjustable assembly in a side by side relationship.

3. A method as defined in claim 1, wherein said filling assemblies include a number of filling members equal to said number of containers.

4. A method as defined in claim 1, wherein said containers comprise vials.

5. A method as defined in claim 3, wherein said filling member comprises a needle.

6. A method as defined in claim 1, further comprising the steps of filling the containers with said filling assembles and sealing the containers after filling the containers with said seal assemblies.

7. A method as defined in claim 1, wherein said seal assemblies are adapted to transmit radiation to seal apertures created by said filling assemblies.

8. A method as defined in claim 7, wherein said seal assemblies each comprise a laser optic device adapted to transmit said radiation.

9. A method as defined in claim 8, wherein said laser optic device includes a laser source.

10. A method as defined in claim 8, wherein said laser optic device is connected to an external laser source.

11. A method as defined in claim 1, wherein the adjustable assembly is adjustable to receive one or more sense assemblies and includes at least one of said sense assemblies.

12. A method as defined in claim 11, further comprising:
    piercing each of said containers with a filling member of the filling assemblies;
    withdrawing said filling member from a respective container; and
    sealing said containers.

13. A method as defined in claim 12, wherein said at least one sense assembly is configured to determine a temperature of an aperture to be sealed on a respective container formed during the piercing step, and further comprising the steps of determining said temperature and determining whether the aperture is sufficiently heated to seal the aperture after the sealing step.

14. A method as defined in claim 11, wherein said at least one sense assembly comprises an infrared sensor.

15. A method as defined in claim 1, wherein said adjustable assembly is configured to releasably retain said filling assemblies and said seal assemblies.

16. A method as defined in claim 1, wherein said filling assemblies are configured to deliver substance into said containers, and further comprising the step of delivering substance respectively into each of said containers.

17. A method as defined in claim 1, wherein each of said filling assemblies comprises a filling member, and further comprising the steps of:
    moving said containers to said adjustable assembly;
    stopping said containers at said adjustable assembly;
    piercing each of said containers with a respective said filling member;
    withdrawing said respective filling member from each of said containers; and
    sealing said containers.

18. A method as defined in claim 1, wherein the one or more filling assemblies and the one or more seal assemblies are located in different stations.

19. A method as defined in claim 1, wherein the one or more seal assemblies are located downstream of the one or more filling assemblies.

20. A method as defined in claim 1, wherein said adjusting step comprises one or more of:
    individually adding at least one of said filling assemblies to the adjustable assembly; or
    individually adding at least one of said seal assemblies to the adjustable assembly.

21. A method as defined in claim 1, wherein said adjustable assembly is adjustable to receive a plurality of filling assemblies and a plurality of seal assemblies;
    wherein each of said one or more filling assemblies comprises a filling member; and
    wherein said adjustable assembly comprises:
        at least one first support and at least one second support laterally spaced relative to said at least one first support, wherein said one or more filling assemblies are supported between said at least one first support and said at least one second support; and
        a drive unit configured to move said filling member of each of said one or more filling assemblies between penetrating and non-penetrating positions.

* * * * *